US012753401B2

(12) United States Patent
Cramer et al.

(10) Patent No.: US 12,753,401 B2
(45) **Date of Patent: *Oct. 6, 2026**

(54) ACETOLACTATE DECARBOXYLASE

(71) Applicant: INTERNATIONAL N&H DENMARK APS, Kongens Lyngby (DK)

(72) Inventors: Jacob Flyvholm Cramer, Højbjerg (DK); Lene Kragh, Højbjerg (DK); Anja Hemmingsen Kellett-Smith, Copenhagen V (DK); Tove Bladt, Skanderborg (DK); Sang-Kyu Lee, Mountain View, CA (US)

(73) Assignee: INTERNATIONAL N&H DENMARK APS, Kongens Lyngby (DK)

( * ) Notice: Subject to any disclaimer, the term of this patent is extended or adjusted under 35 U.S.C. 154(b) by 0 days.

This patent is subject to a terminal disclaimer.

(21) Appl. No.: 18/185,807

(22) Filed: Mar. 17, 2023

(65) Prior Publication Data

US 2023/0332130 A1 Oct. 19, 2023

Related U.S. Application Data

(63) Continuation of application No. 15/574,589, filed as application No. PCT/US2016/033028 on May 18, 2016, now abandoned.

(60) Provisional application No. 62/168,406, filed on May 29, 2015, provisional application No. 62/166,610, filed on May 26, 2015, provisional application No. 62/165,671, filed on May 22, 2015.

(51) Int. Cl.

| | |
|---|---|
| ***C12N 9/96*** | (2006.01) |
| ***C12C 5/00*** | (2006.01) |
| ***C12G 1/022*** | (2006.01) |
| ***C12N 1/38*** | (2006.01) |
| ***C12N 9/88*** | (2006.01) |

(52) U.S. Cl.

CPC .................. *C12N 9/96* (2013.01); *C12C 5/00* (2013.01); *C12C 5/004* (2013.01); *C12G 1/0203* (2013.01); *C12N 1/38* (2013.01); *C12N 9/88* (2013.01); *C12Y 401/01005* (2013.01); *C12G 2200/15* (2013.01)

(58) Field of Classification Search

CPC ........................................................ C12N 9/96

See application file for complete search history.

(56) References Cited

FOREIGN PATENT DOCUMENTS

| | | | |
|---|---|---|---|
| EP | 0128714 | B1 | 8/1989 |
| KR | 100870561 | | 11/2008 |
| WO | 2013092840 | A1 | 6/2013 |
| WO | 2014092562 | A1 | 6/2014 |

OTHER PUBLICATIONS

Chen et al., "Cloning,characterization and application of the promoter region of the alkaline protease gene in Bacillus alcalophillus PB92", IEEE Conferences, Jun. 1, 2009, 3rd International Conference on Bioinformatics and Biomedical Engineering (2009, pp. 1-4).*

Bouton, "Encyclopedia of Beer Brewing", West Sussex, Wiley Blackwell, 2013.

Diderichsen et al., "Cloning of aldB, Which Encodes a-Acetolactate Decarboxylase, an Exoenzyme from Bacillus previs", Journal of Bacteriology, vol. 172, No. 8, Aug. 1990, pp. 4315-4321.

Godtifredsen et al., "Application of the Acetolactate Decarboxylase from Lactobacillus Casei for Accelerated Maturation of Beer", Carlsberg Research Communications, vol. 49, 1984, pp. 69-74.

Guo et al., "Purification and characterization of (alpha)-acetolactate decarboxylase (ALDC) from newly isolated Lactococcus lactis DX", Journal of the Science of Food and Agriculture, vol. 95, No. 8, Sep. 2, 2014, pp. 1655-1661.

Marlow et al., "Structure and Mechanism of Acetolactate Decarboxylase", ACS Chemical Biology, vol. 8, 2013, pp. 2339-2344.

Najmudin et al., "Purification, crystallization and preliminary X-ray crystallographic studies on acetolactate decarboxylase", Acta Crystallographica, vol. 59, Jan. 2003, pp. 1073-1075.

Novozymes Handbook of Brewing, Chapters 1-8, 2013, pp. 1-122.

Ohshiro et al., "Purification and Characterization of o-Acetolactate Decarboxylase from Brevibacterium acetylicum" Agricultural and Biological Chemistry, vol. 53, No. 7, 1989, pp. 1913-1918.

Written Opinion from PCT Application No. PCT/US2016/033028.

* cited by examiner

*Primary Examiner* — Suzanne M Noakes

(57) ABSTRACT

The present disclosure provides methods, compositions, apparatuses and kits comprising ALDC enzymes having a better stability and/or activity, and, optionally, the yield of ALDC enzymes which can be recovered from microorganisms is improved. In some embodiments, the present disclosure provides methods, apparatuses, compositions and kits for the use of metal ions to increase stability and/or activity, and which further can be used to recover the enzymes from microorganisms in improved yields.

2 Claims, 7 Drawing Sheets

Specification includes a Sequence Listing.

ACETOLACTATE DECARBOXYLASE

CROSS-REFERENCE TO RELATED APPLICATIONS

This application is a continuation of U.S. patent application Ser. No. 15/574,589, filed Nov. 16, 2017, which claims priority under 35 USC § 371 as a national phase of International Patent Application No. PCT/US2016/033028, filed May 18, 2016, which claims priority to and the benefit of U.S. provisional patent application Nos. 62/165,671, filed May 22, 2015; 62/166,610, filed May 26, 2015; and 62/168,406, filed May 29, 2015, the contents of each of which are incorporated herein by reference in their entirety.

INCORPORATION BY REFERENCE OF THE SEQUENCE LISTING

The sequence listing provided in the file named NB40736USCNT SequenceListing.xml with a size of 14 KB which was created on Mar. 15, 2023, and which is filed herewith, is incorporated by reference herein in its entirety.

BACKGROUND

Diacetyl is sometimes an unwanted by-product of fermentation processes of carbohydrate containing substances, e.g. wort or grape juice. Formation of diacetyl is most disadvantageous because of its strong and unpleasant smell and in case of beer even small amounts of diacetyl of about 0.10 to 0.15 mg/liter has a negative effect on the flavor and taste of the beer. During the maturation of beer, diacetyl is converted into acetoin by reductases in the yeast cells. Acetoin is with respect to taste and flavor acceptable in beer in much higher concentrations than diacetyl.

Acetolactate decarboxylase (ALDC) can also be used as an enzyme to prevent the formation of diacetyl. α-acetolactate can be converted into acetoin by adding an ALDC enzyme during fermentation. However, ALDC can be unstable at fermenting conditions, especially those of fermenting worts with low malt content.

The purpose of the present invention is to provide ALDC enzymes having a better stability and/or activity, and, optionally, the yield of ALDC enzymes which can be recovered from microorganisms is improved.

SUMMARY OF THE INVENTION

The present disclosure provides compositions and processes for ALDC enzymes.

Aspects and embodiments of the compositions and methods are set forth in the following separately numbered paragraphs.

1. A composition comprising an acetolactate decarboxylase (ALDC) enzyme and zinc, where the zinc is present at a concentration of about 1 μM to about 200 mM.

2. The composition of paragraph 1, where the zinc is present at a concentration of about 10 μM to about 150 mM, or about 20 μM to about 120 mM, or about 25 μM to about 100 mM, or about 25 μM to about 50 mM, or about 25 μM to about 20 mM, or about 25 μM to about 50 μM, or about 100 μM to about 20 mM, or about 250 μM to about 20 mM, or about 500 μM to about 20 mM, or about 1 mM to about 20 mM, or about 1 mM to about 10 mM, or about 1 mM to about 5 mM.

3. The composition of any preceding paragraph, where the zinc is present at a concentration of about 100 μM to about 10 mM.

4. The composition of any preceding paragraph, where the zinc is present at a concentration of about 1 mM to about 5 mM. The composition of any preceding paragraph, wherein the molar ratio of zinc to ALDC enzyme is higher than 1; or 2:1 or higher; or 10:1 or higher; or 20:1 or higher; or 30:1 or higher; or 60:1 or higher.

5. The composition of any preceding paragraph, where the ALDC enzyme is an ALDC derivative.

6. The composition of paragraph 5, where the ALDC derivative is an ALDC enzyme treated with glutaraldehyde.

7. The composition of paragraph 6, where the ALDC enzyme is treated with glutaraldehyde at a concentration corresponding to about 0.1 to about 5 g of glutaraldehyde per g of pure ALDC enzyme.

8. The composition of any preceding paragraph, where the activity of the ALDC enzyme is in the range of 950 to 2500 Units per mg of protein.

9. The composition of any preceding paragraph, where the activity of the ALDC enzyme is in the range of 1000 to 2500 Units per mg of protein.

10. The composition of any preceding paragraph further comprising at least one additional enzyme or enzyme derivative selected from the group consisting of acetolactate reductoisomerases, acetolactate isomerases, amylase, glucoamylase, hemicellulase, cellulase, glucanase, pullulanase, isoamylase, endo-glucanase and related beta-glucan hydrolytic accessory enzymes, xylanase, xylanase accessory enzymes (for example, arabinofuranosidase, ferulic acid esterase, and xylan acetyl esterase) and protease.

11. The composition of any preceding paragraph, where the ALDC enzyme is from *Lactobacillus casei, Brevibacterium acetylicum, Lactococcus lactis, Leuconostoc lactis, Enterobacter aerogenes, Bacillus subtilis, Bacillus brevis, Lactococcus lactis* DX, or *Bacillus licheniformis.*

12. The composition of any preceding paragraph, where the ALDC enzyme is from *Bacillus brevis* or *Bacillus licheniformis.*

13. The composition of any preceding paragraph, where the ALDC enzyme has an amino acid sequence having at least 80% identity with any one selected from SEQ ID NO: 2, SEQ ID NO: 3, SEQ ID NO: 5, SEQ ID NO: 7 and SEQ ID NO: 8 or any functional fragment thereof.

14. Use of the composition according to any preceding paragraph in fermentation (such as beer and/or wine and/or cider and/or perry and/or sake fermentation).

15. A method for increasing the activity and/or stability of an ALDC enzyme comprising adding zinc at a concentration of about 1 μM to about 200 mM. The method of paragraph 15 for increasing the activity and/or stability of an ALDC enzyme in a composition comprising ALDC wherein said method comprises the step of adding zinc to the composition so that said zinc is present in said composition at a concentration of about 1 μM to about 200 mM.

16. The method of paragraph 15, where the zinc is present in said composition at a concentration of about 1 μM to about 300 μM, or about 6 μM to about 300 μM, or about 1 μM to about 50 μM; or about 1 μM to about 25 μM, or about 10 μM to about 150 mM, or about 20 μM to about 120 mM, or about 25 μM to about 100 mM, or about 25 μM to about 50 mM, or about 25 μM to about 20 mM, or about 25 μM to about 50 μM, or about 100 μM to about 20 mM, or about 250 μM to about 20 mM, or about 500 μM to about 20 mM, or about 1 mM to about 20 mM, or about 1 mM to about 10 mM, or about 1 mM to about 5 mM.

17. The method of paragraphs 15 or 16, where the zinc is present in said composition at a concentration of about 100 μM to about 10 mM.

18. The method of paragraphs 15 or 16, where the zinc is present in said composition at a concentration of about 1 mM to about 5 mM. The method of paragraphs 15 or 16, where the molar ratio of zinc to ALDC enzyme is higher than 1; or 2:1 or higher; or 10:1 or higher; or 20:1 or higher; or 30:1 or higher; or 60:1 or higher in said composition.

19. The method of paragraph 15 where the zinc is added to a cultivation media as a supplement during the production of the ALDC enzyme by an ALDC producing host cell. A method for increasing the activity and/or stability of an ALDC enzyme in a cultivation media comprising an ALDC producing host cell wherein said method comprises the step of adding zinc to the cultivation media as a supplement during the production of the ALDC enzyme by the ALDC producing host cell.

20. The method of paragraph 19, where the zinc is added at a concentration of 1 μM to about 1 mM.

21. The method of paragraph 20, where the zinc is added at a concentration of 25 μM to about 150 μM, or about 60 μM to about 150 μM.

22. The method of any one of paragraphs 19-21, where the host cell is a *Bacillus* host cell.

23. The method of paragraph 22, where the *Bacillus* host cell is *Bacillus subtilis.*

24. The method of paragraph 15, where the zinc is added in a fermentation media and/or maturation media during fermentation of a beverage (such as beer and/or wine and/or cider and/or perry and/or sake fermentation). A method for increasing the activity and/or stability of an ALDC enzyme in a fermentation media and/or maturation media comprising an ALDC producing host cell wherein said method comprises the step adding zinc to the fermentation media and/or maturation media during fermentation of a beverage (such as beer and/or wine and/or cider and/or perry and/or sake fermentation).

25. The method of paragraph 24, where the zinc is added at a concentration of about 1 μM to about 300 μM, or about 6 μM to about 300 μM, or about 1 μM to about 50 μM; or about 1 μM to about 25 μM.

26. The method of any one of paragraphs 24, 25 and the current paragraph, where the zinc is added as a composition comprising ALDC and zinc, wherein the zinc is present in the composition at a concentration of 1 mM to about 5 mM. The method of any one of paragraphs 24, 25 and the current paragraph, where the zinc is added as a composition comprising ALDC and zinc, where the molar ratio of zinc to ALDC enzyme in the composition is higher than 1; or 2:1 or higher; or 10:1 or higher; or 20:1 or higher; or 30:1 or higher; or 60:1 or higher.

27. A cultivation media for an ALDC producing host cell comprising zinc at a concentration of about 1 μM to about 1 mM; preferably said cultivation media comprises an ALDC producing host cell.

28. The cultivation media of paragraph 27, comprising zinc at concentration of about 25 μM to about 150 μM.

29. The cultivation media of paragraph 27, where the zinc is added at a concentration of 60 μM to about 150 μM.

30. A beer and/or wine and/or cider and/or perry and/or sake fermentation media and/or maturation media comprising an ALDC enzyme and zinc at a concentration of about 0.1 μM to about 200 mM, A beer and/or wine and/or cider and/or perry and/or sake fermentation media and/or maturation media comprising a composition comprising an ALDC enzyme and zinc wherein said composition comprises zinc at a concentration of about 0.1 μM to about 200 mM, preferably 1 μM to about 200 mM.

31. The beer and/or wine and/or cider and/or perry and/or sake fermentation media and/or maturation of paragraph 30, wherein said composition comprises zinc at a concentration of about 0.1 μM to about 300 μM, preferably 1 μM to about 300 μM. The beer and/or wine and/or cider and/or perry and/or sake fermentation media and/or maturation of paragraph 30, comprising wherein said composition comprises zinc at a concentration of about 6 μM to about 300 μM, or about 1 μM to about 50 μM, or about 6 μM to about 50 μM, or about 6 μM to about 25 μM. The beer and/or wine and/or cider and/or perry and/or sake fermentation media and/or maturation of paragraph 30 and the current paragraph, where the zinc and the ALDC enzyme are added in a composition, wherein the zinc is present in the composition at a concentration of about 1 mM to about 20 mM, such as 1 mM to about 5 mM. The beer and/or wine and/or cider and/or perry and/or sake fermentation media and/or maturation of paragraph 30 or the current paragraph, where the zinc and the ALDC enzyme are added in a composition, where the molar ratio of zinc to ALDC enzyme in the composition is higher than 1; or 2:1 or higher; or 10:1 or higher; or 20:1 or higher; or 30:1 or higher; or 60:1 or higher.

32. The beer and/or wine and/or cider and/or perry and/or sake fermentation media and/or maturation of paragraph 30 or 31, where the activity of the ALDC enzyme is in the range of 1000 to 2500 Units per mg of protein.

33. The beer and/or wine and/or cider and/or perry and/or sake fermentation media and/or maturation of any one of paragraphs 30-32, further comprising at least one additional enzyme or enzyme derivative selected from the group consisting of acetolactate reductoisomerases, acetolactate isomerases, amylase, glucoamylase, hemicellulase, cellulase, glucanase, pullulanase, isoamylase, endo-glucanase and related beta-glucan hydrolytic accessory enzymes, xylanase, xylanase accessory enzymes (for example, arabinofuranosidase, ferulic acid esterase, and xylan acetyl esterase) and protease.

34. A composition comprising an ALDC enzyme, where the ALDC enzyme is in the range of 1000 to 2500 Units per mg of protein.

35. The composition of paragraph 34, where the ALDC enzyme is from *Lactobacillus casei, Brevibacterium acetylicum, Lactococcus lactis, Leuconostoc lactis, Enterobacter aerogenes, Bacillus subtilis, Bacillus brevis, Lactococcus lactis* DX, or *Bacillus licheniformis.*

36. The composition of paragraph 34, where the ALDC enzyme is from *Bacillus brevis* or *Bacillus licheniformis.*

37. The composition of any one of paragraphs 34-36, where the ALDC enzyme has an amino acid sequence having at least 80% identity with any one selected from SEQ ID NO: 2, SEQ ID NO: 3, SEQ ID NO: 5, SEQ ID NO: 7 and SEQ ID NO: 8 or any functional fragment thereof.

38. The composition of any one of paragraphs 34-37, where zinc is present at a concentration of about 1 μM to about 200 mM, preferably about 100 μM to about 200 mM. The composition of any one of paragraphs 34-37, where the molar ratio of zinc to ALDC enzyme in the composition is higher than 1; or 2:1 or higher; or 10:1 or higher; or 20:1 or higher; or 30:1 or higher; or 60:1 or higher.

39. A method for beer and/or wine and/or cider and/or perry and/or sake production comprising adding an ALDC enzyme and zinc during the beer and/or wine and/or cider and/or perry and/or sake production, where the zinc is present at a concentration of about 0.1 μM to about 300 μM, preferably 1 μM to about 300 μM. The method of paragraph 39 for beer and/or wine and/or cider and/or perry and/or sake production comprising adding an ALDC enzyme and adding zinc to a media (such as a fermentation and/or a maturation media) for the beer and/or wine and/or cider and/or perry and/or sake during said beer and/or wine and/or cider and/or perry and/or sake production so that said zinc is present in said media at a concentration of about 0.1 μM to about 300 μM, such as about 6 μM to about 300 μM.

40. The method of paragraph 39, where the zinc is present in said media at a concentration of about 0.1 μM to about 50 μM. The method of paragraph 39, where the zinc is present in said media at a concentration of about 6 μM to about 300 μM, or 1 μM to about 50 μM, or about 6 μM to about 50 μM, or about 6 μM to about 25 μM.

41. The method of paragraph 39, where the zinc and the ALDC enzyme are added in a composition, wherein zinc is present in said composition at a concentration of about 1 mM to about 5 mM. The method of paragraph 39, where the zinc and the ALDC enzyme are added in a composition, where the molar ratio of zinc to ALDC enzyme in the composition is higher than 1; or 2:1 or higher; or 10:1 or higher; or 20:1 or higher; or 30:1 or higher; or 60:1 or higher. A method for beer and/or wine and/or cider and/or perry and/or sake production comprising adding a composition comprising an ALDC enzyme and zinc to a media (such as a fermentation and/or a maturation media) for the beer and/or wine and/or cider and/or perry and/or sake during said beer and/or wine and/or cider and/or perry and/or sake production wherein (i) zinc is present in the composition at a concentration of about 1 μM to about 200 mM, preferably about 1 mM to about 5 mM; or (ii) the molar ratio of zinc to ALDC enzyme in the composition is higher than 1; or 2:1 or higher; or 10:1 or higher; or 20:1 or higher; or 30:1 or higher; or 60:1 or higher.

42. The method of any one of paragraphs 39-41, where the ALDC enzyme and the zinc are added during a fermentation process or a maturation process.

43. The method of any one of paragraphs 39-42, where the ALDC enzyme is added at a concentration of about 0.5 g to about 10 g per hectoliter of beer and/or wine and/or cider and/or perry and/or sake ferment.

44. The method of any one of paragraphs 39-43, where the ALDC enzyme is added at a concentration of about 1 g to about 5 g per hectoliter of beer and/or wine and/or cider and/or perry and/or sake ferment.

45. The method of any one of paragraphs 39-44, where the activity of the ALDC enzyme is in the range of 1000 to 2500 Units per mg of protein.

46. The method of any one of paragraphs 39-45, where the ALDC enzyme is from *Lactobacillus casei, Brevibacterium acetylicum, Lactococcus lactis, Leuconostoc lactis, Enterobacter aerogenes, Bacillus subtilis, Bacillus brevis, Lactococcus lactis* DX, or *Bacillus licheniformis.*

47. The method of any one of paragraphs 39-45, where the ALDC enzyme is from *Bacillus brevis* or *Bacillus licheniformis.*

48. The method of any one of paragraphs 39-45, where the ALDC enzyme has an amino acid sequence having at least 80% identity with any one selected from SEQ ID NO: 2, SEQ ID NO: 3, SEQ ID NO: 5, SEQ ID NO: 7 and SEQ ID NO: 8 or any functional fragment thereof.

49. A method for increasing the activity and/or stability of an ALDC enzyme comprising adding a metal ion at a concentration of about 1 μM to about 200 mM, preferably about 100 μM to about 200 mM. The method of paragraph 49 for increasing the activity and/or stability of an ALDC enzyme in a composition comprising ALDC wherein said method comprises the step of adding a metal ion to the composition at a concentration of about 1 μM to about 200 mM, preferably about 100 μM to about 200 mM.

50. The method of paragraph 49, where the atomic radius for the metal ion is about 140 pm to about 165 pm.

51. The method of paragraph 50, where the atomic radius for the metal ion is about 140 pm to about 150 pm.

52. The method of paragraph 51, where the atomic radius for the metal ion is about 142 pm to about 146 pm.

53. The method of paragraph 49, where the metal ion is selected from the group consisting of $Zn^{2+}$, $Mg^{2+}$, $Mn^{2+}$, $Co^{2+}$, $Cu^{2+}$, $Ca^{2+}$, $Ba^{2+}$ and $Fe^{2+}$ and combinations thereof.

54. The method of paragraph 53, where the metal ion is selected from the group consisting of $Zn^{2+}$, $Mn^{2+}$, and $Co^{2+}$.

55. The method of paragraph 54, where the metal ion is $Zn^{2+}$.

56. The method of any one of paragraphs 49-55, where the ALDC enzyme is from *Lactobacillus casei, Brevibacterium acetylicum, Lactococcus lactis, Leuconostoc lactis, Enterobacter aerogenes, Bacillus subtilis, Bacillus brevis, Lactococcus lactis* DX, or *Bacillus licheniformis.*

57. The method of any one of paragraphs 49-55, where the ALDC enzyme is from *Bacillus brevis* or *Bacillus licheniformis.*

58. The method of any one of paragraphs 49-55, where the ALDC enzyme has an amino acid sequence having at least 80% identity with any one selected from SEQ ID NO: 2, SEQ ID NO: 3, SEQ ID NO: 5, SEQ ID NO: 7 and SEQ ID NO: 8 or any functional fragment thereof.

59. A composition comprising an acetolactate decarboxylase (ALDC) enzyme and a metal ion, where the metal ion is present at a concentration of about 1 μM to about 200 mM, preferably about 100 μM to about 200 mM.

60. The composition of paragraph 59, where the atomic radius for the metal ion is about 140 pm to about 165 pm.

61. The composition of paragraphs 59, where the atomic radius for the metal ion is about 140 pm to about 150 pm.

62. The composition of paragraph 61, where the atomic radius for the metal ion is about 142 pm to about 146 pm.

63. The composition of paragraph 59, where the metal ion is selected from the group consisting of $Zn^{2+}$, $Mg^{2+}$, $Mn^{2+}$, $Co^{2+}$, $Cu^{2+}$, $Ca^{2+}$, $Ba^{2+}$ and $Fe^{2+}$ and combinations thereof.

64. The composition of paragraph 63, where the metal ion is selected from the group consisting of $Zn^{2+}$, $Mn^{2+}$, and $Co^{2+}$.

65. The composition of paragraph 64, where the metal ion is $Zn^{2+}$.

66. A method for decomposing acetolactate comprising the step of treating a substrate with an ALDC enzyme and a metal ion, where the metal ion is present at a concentration of about 1 μM to about 200 mM. The method of paragraph 66 for decomposing acetolactate comprising the step of treating a substrate with a composition comprising an ALDC enzyme and a metal ion so that the metal ion is present in said composition at a concentration of about 1 μM to about 200 mM. Preferably said substrate is a carbohydrate containing substrate such as a wort or a fruit juice. Preferably said substrate is a fermentation and/or maturation media.

67. The method of paragraph 66, where the metal ion is present in said composition at a concentration of about 10 μM to about 150 mM, or about 20 μM to about 120 mM, or about 25 μM to about 100 mM, or about 25 μM to about 50 mM, or about 25 μM to about 20 mM, or about 100 μM to about 20 mM, or about 250 μM to about 20 mM, or about 1 mM to about 20 mM, or about 1 mM to about 5 mM.

68. The method of paragraph 66, where the metal ion is present in said substrate (such as a fermentation and/or maturation media) at a concentration of about 1 μM to about 500 μM, or about 1 μM to about 300 μM, or about 6 μM to about 300 μM, or about 1 μM to about 100 μM, or about 1 μM to about 50 μM, or about 1 μM to about 25 μM, or about 6 μM to about 50 μM, or about 6 μM to about 25 μM, or about 25 μM to about 50 μM.

69. The method of paragraph 66, where the metal ion and the ALDC are added in a composition, wherein said metal ion is present in said composition at a concentration of about 1 mM to about 5 mM. The method of paragraph 66, where the metal ion and the ALDC are added in a composition, where the molar ratio of the metal ion to ALDC enzyme in the composition is higher than 1; or 2:1 or higher; or 10:1 or higher; or 20:1 or higher; or 30:1 or higher; or 60:1 or higher.

70. The method of any one of paragraphs 66-69, where the metal ion is selected from the group consisting of $Zn^{2+}$, $Mg^{2+}$, $Mn^{2+}$, $Co^{2+}$, $Cu^{2+}$, $Ca^{2+}$, $Ba^{2+}$ and $Fe^{2+}$ and combinations thereof.

71. The method of any one of paragraphs 66-70, where the metal ion is selected from the group consisting of $Zn^{2+}$, $Mn^{2+}$, and $Co^{2+}$.

72. The method of any one of paragraphs 66-71, where the metal ion is $Zn^{2+}$.

73. The method of any one of paragraphs 66-72, where the substrate is treated during a beer and/or wine and/or cider and/or perry and/or sake fermentation or maturation process.

74. The method of any one of paragraphs 66-72, where the ALDC enzyme is from *Lactobacillus casei, Brevibacterium acetylicum, Lactococcus lactis, Leuconostoc lactis, Enterobacter aerogenes, Bacillus subtilis, Bacillus brevis, Lactococcus lactis* DX, or *Bacillus licheniformis.*

75. The method of any one of paragraphs 66-72, where the ALDC enzyme is from *Bacillus brevis* or *Bacillus licheniformis.*

76. The method of any one of paragraphs 66-72, where the ALDC enzyme has an amino acid sequence having at least 80% identity with any one selected from SEQ ID NO: 2, SEQ ID NO: 3, SEQ ID NO: 5, SEQ ID NO: 7 and SEQ ID NO: 8 or any functional fragment thereof.

BRIEF DESCRIPTION OF THE DRAWINGS

A better understanding of the features and advantages of the present invention will be obtained by reference to the following detailed description that sets forth illustrative embodiments, in which the principles of the invention are utilized, and the accompanying drawings of which.

DETAILED DESCRIPTION OF THE INVENTION

Figure 1:
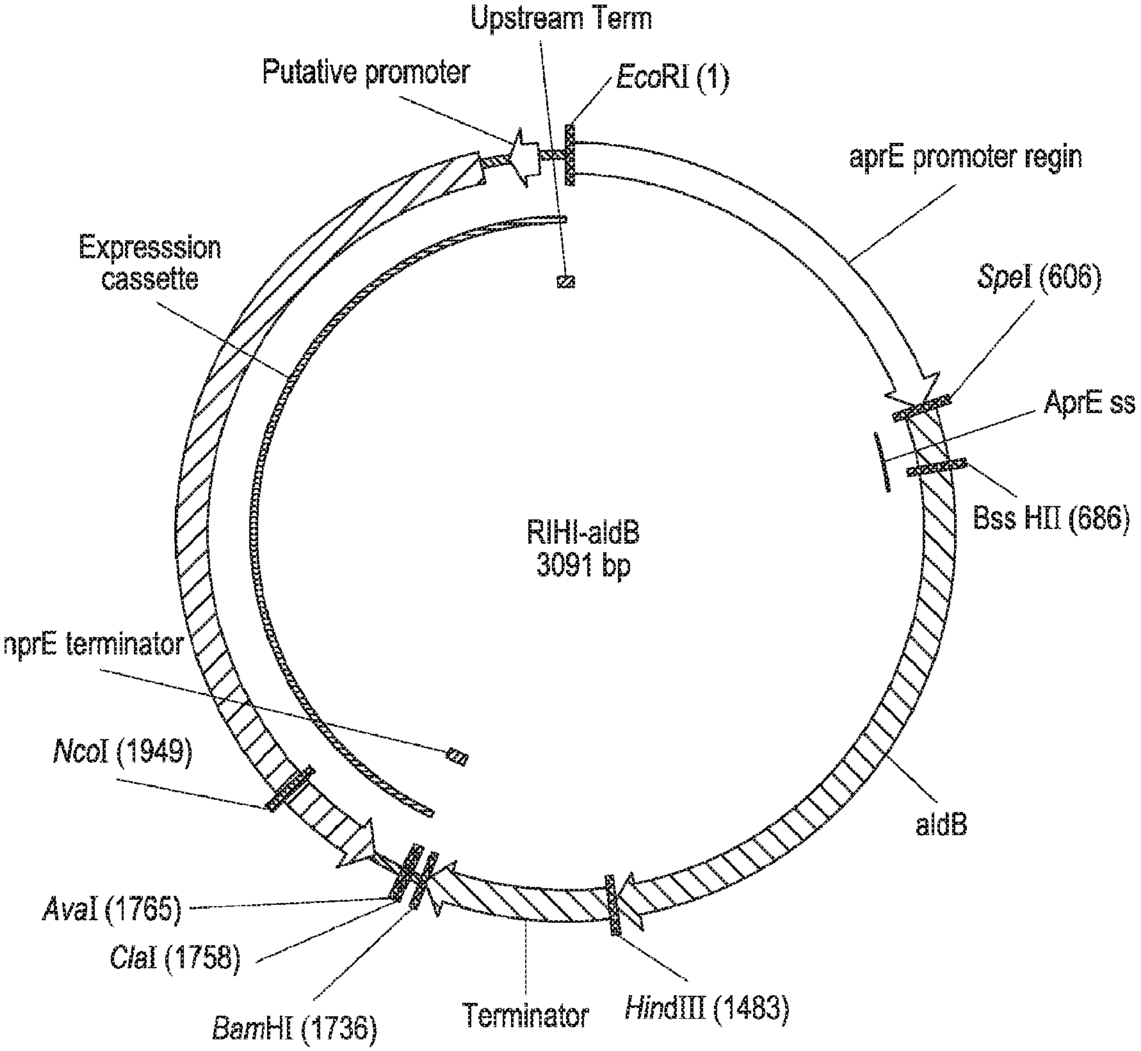
FIG. 1 shows a plasmid map of alrA(CB)RIHI-aldB for expression of Acetolactate Decarboxylase, aldB

The present disclosure provides methods, compositions, apparatuses and kits comprising ALDC enzymes having a better stability and/or activity, and, optionally, the yield of ALDC enzymes which can be recovered from microorganisms is improved. In some embodiments, the present disclosure provides methods, apparatuses, compositions and kits for the use of metal ions to increase stability and/or activity, and, optionally, which further can be used to recover the enzymes (e.g. ALDC enzymes) from microorganisms in improved yields.

Unless defined otherwise, all technical and scientific terms used herein have the same meaning as commonly understood by one of ordinary skill in the art to which this disclosure belongs. Singleton, et al., DICTIONARY OF MICROBIOLOGY AND MOLECULAR BIOLOGY, 20 ED., John Wiley and Sons, New York (1994), and Hale & Marham, THE HARPER COLLINS DICTIONARY OF BIOLOGY, Harper Perennial, NY (1991) provide one of skill with a general dictionary of many of the terms used in this disclosure.

This disclosure is not limited by the exemplary methods and materials disclosed herein, and any methods and materials similar or equivalent to those described herein can be used in the practice or testing of embodiments of this disclosure. Numeric ranges are inclusive of the numbers defining the range. Unless otherwise indicated, any nucleic acid sequences are written left to right in 5' to 3' orientation; amino acid sequences are written left to right in amino to carboxy orientation, respectively.

The headings provided herein are not limitations of the various aspects or embodiments of this disclosure which can be had by reference to the specification as a whole. Accordingly, the terms defined immediately below are more fully defined by reference to the specification as a whole.

It must be noted that as used herein and in the appended claims, the singular forms "a", "an", and "the" include plural referents unless the context clearly dictates otherwise. Thus, for example, reference to "a protease" includes a plurality of such enzymes and reference to "the feed" includes reference to one or more feeds and equivalents thereof known to those skilled in the art, and so forth.

The publications discussed herein are provided solely for their disclosure prior to the filing date of the present application. Nothing herein is to be construed as an admission that such publications constitute prior art to the claims appended hereto.

All patents and publications referred to herein are incorporated by reference.

ALDC

In some aspects the invention provides ALDC enzymes having a better stability and/or activity, and, optionally, the yield of ALDC enzymes which can be recovered from microorganisms is improved. The terms "better stability" and "increased stability" as used herein refer to an ALDC enzyme whose ALDC activity is maintained for a longer period of time when in the presence of a metal ion (such as $Zn^{2+}$) when compared to the ALDC activity of the enzyme in the absence of the metal ion. The terms "better activity" and "increased activity" as used herein refer to an ALDC enzyme having an increased ALDC activity when in the presence of a metal ion (such as $Zn^{2+}$) when compared to the ALDC activity of the enzyme in the absence of the metal ion. The term "improved" in connection to the yield of ALDC enzyme refers to an increase in the ALDC activity which is produced when a host microorganism is in the presence of a metal ion (such as $Zn^{2+}$) compared to the ALDC activity produced when the host microorganism is in the absence of the metal ion. Without wishing to be bound by theory, the metal ion (such as $Zn^{2+}$) can be added during and/or after the culture process (e.g. ALDC production) in order to increase stability and/or increase activity and/or to increase yield of ALDC enzymes. The terms "host cell", "host microorganism", "strain" and "microorganism" may be used interchangeably herein.

Acetolactate decarboxylase (ALDC) is an enzyme that belongs to the family of carboxy lyases, which are responsible for cleaving carbon-carbon bonds. Acetolactate decarboxylase catalyzes the conversion of 2-acetolactate (also known as 2-hydroxy-2-methyl-3-oxobutanoate) to 2-acetoin and releases $CO_2$. The terms "ALDC" and "ALDC enzyme" may be used interchangeably herein.

Acetolactate decarboxylase enzymes catalyze the enzymatic reaction belonging to the classification EC 4.1.1.5 (acetolactate decarboxylase activity) and gene ontology (GO) term ID of GO: 0047605. The GO term ID specifies that any protein characterized as having this associated GO term encodes an enzyme with catalytic acetolactate decarboxylase activity.

Various acetolactate decarboxylase genes (such as alsD or aldB), which encode acetolactate decarboxylase enzymes, are known in the art. The alsD gene, which encodes ALDC enzyme, may be derived or derivable from *Bacillus subtilis*. The aldB gene, which encodes ALDC enzyme, may be derived or derivable from *Bacillus brevis*. The alsD gene, which encodes ALDC enzyme, may be derived or derivable from *Bacillus licheniformis*. UNIPROT accession number Q65E52.1 is an example of an ALDC enzyme. UNIPROT accession number Q65E52.1 is an example of an ALDC enzyme derived or derivable from *Bacillus licheniformis*. Examples of acetolactate decarboxylase genes include but are not limited to gi|375143627|ref|YP_005006068.1| acetolactate decarboxylase [*Niastella koreensis* OR20-10]; gi|361057673|gb|AEV96664.1| acetolactate decarboxylase [*Niastella koreensis* OR20-10]; gi|218763415|gb|ACL05881.1| acetolactate decarboxylase [*Desulfatibacillum alkenivorans* AK-01]; gi|220909520|ref|YP_002484831.1| acetolactate decarboxylase [Cyanothece sp. PCC 7425]; gi|218782031|ref|YP_002433349.1| acetolactate decarboxylase [*Desulfatibacillum alkenivorans* AK-01]; gi|213693090|ref|YP_002323676.1| acetolactate decarboxylase [*Bifidobacterium longum* subsp. *infantis* ATCC 15697=JCM 1222]; gi|189500297|ref|YP_001959767.1 acetolactate decarboxylase [*Chlorobium phaeobacteroides* BS1]; gi|189423787|ref|YP_001950964.1| acetolactate decarboxylase [*Geobacter lovleyi* SZ]; gi|172058271|ref|YP_001814731.1| acetolactate decarboxylase [*Exiguobacterium sibiricum* 255-15]; gi|163938775|ref|YP_001643659.1| acetolactate decarboxylase [*Bacillus weihenstephanensis* KBAB4]; gi|158522304|ref|YP_001530174.1| acetolactate decarboxylase [*Desulfococcus oleovorans* Hxd3]; gi|57371670|ref|YP_001479659.1| acetolactate decarboxylase [*Serratia proteamaculans* 568]; gi|150395111|ref|YP_001317786.1| acetolactate decarboxylase [*Staphylococcus aureus* subsp. *aureus* JH1]; gi|150394715|ref|YP_001317390.1| acetolactate decarboxylase [*Staphylococcus aureus* subsp. *aureus* JH1]; gi|146311679|ref|YP_001176753.1 acetolactate decarboxylase [*Enterobacter* sp. 638]; gi|109900061|ref|YP_663316.1| acetolactate decarboxylase [*Pseudoalteromonas atlantica* T6c]; gi|219866131|gb|ACL46470.1| acetolactate decarboxylase [Cyanothece sp. PCC 7425]; gi|213524551|gb|ACJ53298.1| acetolactate decarboxylase [*Bifidobacterium longum* subsp. *infantis* ATCC 15697=JCM 1222]; gi|189420046|gb|ACD94444.1| acetolactate decarboxylase [*Geobacter lovleyi* SZ]; gi|158511130|gb|ABW68097.1| acetolactate decarboxylase [*Desulfococcus oleovorans* Hxd3]; gi|157323434|gb|ABV42531.1| acetolactate decarboxylase [*Serratia proteamaculans* 568]; gi|145318555|gb|ABP60702.1| acetolactate decarboxylase [*Enterobacter* sp. 638]; gi|149947563|gb|ABR53499.1| acetolactate decarboxylase [*Staphylococcus aureus* subsp. *aureus* JH1]; gi|149947167|gb|ABR53103.1| acetolactate decarboxylase [*Staphylococcus aureus* subsp. *aureus* JH1]; gi|163860972|gb|ABY42031.1| Acetolactate decarboxylase [*Bacillus weihenstephanensis* KBAB4]; gi|109702342|gb|ABG42262.1| Acetolactate decarboxylase [*Pseudoalteromonas atlantica* T6c]; gi|189495738|gb|ACE04286.1| acetolactate decarboxylase [*Chlorobium phaeobacteroides* BS1]; gi|171990792|gb|ACB61714.1| acetolactate decarboxylase [*Exiguobacterium sibiricum* 255-15]; gi|223932563|ref|ZP03624564.1 acetolactate decarboxylase [*Streptococcus suis* 89/1591]; gi|194467531|ref|ZP03073518.1| acetolactate decarboxylase [*Lactobacillus reuteri* 100-23]; gi|223898834|gb|EEF65194.1| acetolactate decarboxylase [*Streptococcus suis* 89/1591]; gi|194454567|gb|EDX43464.1| acetolactate decarboxylase [*Lactobacillus reuteri* 100-23]; gi|384267135|ref|YP_005422842.1| acetolactate decarboxylase [*Bacillus amyloliquefaciens* subsp. *plantarum* YAU B9601-Y2]; gi|375364037|ref|YP_005132076.1| acetolactate decarboxylase [*Bacillus amyloliquefaciens* subsp. *plantarum* CAU B946]; gi|34079323|ref|YP_004758694.1| acetolactate decarboxylase [*Corynebacterium variabile* DSM 44702]; gi|336325119|ref|YP_004605085.1| acetolactate decarboxylase [*Corynebacterium resistens* DSM 45100]; gi|148269032|ref|YP_001247975.1| acetolactate decarboxylase [*Staphylococcus aureus* subsp. *aureus* JH9]; gi|148268650|ref|YP_001247593.1| acetolactate decarboxylase [*Staphylococcus aureus* subsp. *aureus* JH9]; gi|1485433721|ref|YP_001270742.1| acetolactate decarboxylase [*Lactobacillus reuteri* DSM 20016];

gi|380500488|emb|CCG51526.1| acetolactate decarboxylase [*Bacillus amyloliquefaciens* subsp. *plantarum* YAU B9601-Y2]; gi|371570031|emb|CCF06881.1| acetolactate decarboxylase [*Bacillus amyloliquefaciens* subsp. *plantarum* CAU B946]; gi|340533141|gb|AEK35621.1| acetolactate decarboxylase [*Corynebacterium variabile* DSM 44702]; gi|336101101|gb|AE108921.1| acetolactate decarboxylase [*Corynebacterium resistens* DSM 45100]; gi|148530406|gb|ABQ82405.1| acetolactate decarboxylase [*Lactobacillus reuteri* DSM 20016]; gi|147742101|gb|ABQ50399.1| acetolactate decarboxylase [*Staphylococcus aureus* subsp. *aureus* JH9]; gi|147741719|gb|ABQ50017.1| acetolactate decarboxylase [*Staphylococcus aureus* subsp. *aureus* JH9]; gi|392529510|ref|ZP10276647.1| acetolactate decarboxylase [*Carnobacterium maltaromaticum* ATCC 35586]; gi|366054074|ref|ZP09451796.1| acetolactate decarboxylase [*Lactobacillus suebicus* KCTC 3549]; gi|339624147|ref|ZP08659936.1| acetolactate decarboxylase [*Fructobacillus jructosus* KCTC 3544]; and gi|336393727|ref|ZP08575126.1| acetolactate decarboxylase [*Lactobacillus coryniformis* subsp. *torquens* KCTC 3535]. UNIPROT Accession No. P23616.1 (Diderichsen et al., J Bacteriol. (1990) 172(8): 4315) is an example of an ALDC enzyme. UNIPROT accession number P23616.1 is an example of an ALDC enzyme derived or derivable from *Bacillus brevis*. Each sequence associated with the foregoing accession numbers is incorporated herein by reference.

In some embodiments, the invention relates to ALDC enzymes from *Lactobacillus casei* (Godtfredsen 1984), *Brevibacterium acetylicum* (Oshiro, 1989), *Lactococcus lactis* (Vincent Phalip 1994), *Leuconostoc lactis* (O sulivan, 2001), *Enterobacter aerogenes* (Blomquist, 1993), *Bacillus subtilis* (Renna, 1993), *Bacillus brevis* (Svendsen, 1989) and *Lactococcus lactis* DX (Yuxing, 2014). In some embodiments, the ALDC enzyme is from *Lactobacillus casei, Brevibacterium acetylicum, Lactococcus lactis, Leuconostoc lactis, Enterobacter aerogenes, Bacillus subtilis, Bacillus brevis, Lactococcus lactis* DX, or *Bacillus licheniformis*. As used herein, the term "ALDC enzyme is from" refers to the ALDC enzyme being derived or derivable from.

It is to be understood that any suitable ALDC enzymes, i.e. ALDC produced from any microorganism which activity is dependent on metal ions, can be used according to the invention. In some embodiments, the ALDC used in the methods and compositions described herein is an ALDC from *Bacillus brevis* or *Bacillus licheniformis*.

The ALDC activity of the enzyme composition according to the invention is measured by the ALDC assays as described herein or any suitable assay known in the art. The standard assay is carried out at pH 6.0, and it can be performed at different pH values and temperatures for the additional characterization and specification of enzymes.

One unit of ALDC activity is defined as the amount of enzyme which produces 1 μmole acetoin per minute under the conditions of the assay (e.g., pH 6.0 (or as specified) and 30° C.).

In some embodiments, the ALDC is an ALDC derivative. In some embodiments, the ALDC derivative is characterized by the fact that ALDC in an aqueous medium is treated with or has been treated with glutaraldehyde. In some embodiments, the ALDC is treated with or has been treated with glutaraldehyde in a concentration corresponding to between 0.1 and 5 g of glutaraldehyde per g of pure ALDC protein, preferably corresponding to between 0.25 and 2 g of glutaraldehyde per g of pure ALDC protein.

In some embodiments, the ALDC enzyme comprises an amino acid sequence having at least 70%, 75%, 80%, 85%, 90%, 95%, 97%, 98%, 99% or 100% identity with SEQ ID NO: 2, SEQ ID NO: 3, SEQ ID NO: 5, SEQ ID NO: 7, or SEQ ID NO: 8 or any functional fragment thereof. One aspect of the invention relates to an enzyme exhibiting ALDC activity, which enzyme comprises an amino acid sequence having at least 80% identity with any one selected from SEQ ID NO: 2, SEQ ID NO: 3, SEQ ID NO: 5, SEQ ID NO: 7, SEQ ID NO: 8 or any functional fragment thereof. In some embodiments, the ALDC enzyme is encoded by a nucleic acid sequence having at least 70%, 75%, 80%, 85%, 90%, 95%, 97%, 98%, 99% or 100% identity with SEQ ID NO: 1, SEQ ID NO: 4, or SEQ ID NO: 6 or any functional fragment thereof.

In some embodiments, the enzyme has a temperature optimum in the range of 5-80° C., such as in the range of 5-40° C. or 15-80° C., such as in the range 20-80° C., such as in the range 5-15° C., 10-40° C., 10-50° C., 15-20° C., 45-65° C., 50-65° C., 55-65° C. or 60-80° C. In some embodiments, the enzyme has a temperature optimum of about 60° C.

In some embodiments, the enzyme has a total number of amino acids of less than 350, such as less than 340, such as less than 330, such as less than 320, such as less than 310, such as less than 300 amino acids, such as in the range of 200 to 350, such as in the range of 220 to 345 amino acids.

In some embodiments, the amino acid sequence of the enzyme has at least one, two, three, four, five, six, seven, eight, nine or ten amino acid substitutions as compared to any one amino acid sequence selected from SEQ ID NO: 2, SEQ ID NO: 3, SEQ ID NO: 5, SEQ ID NO: 7, SEQ ID NO: 8, or any functional fragment thereof.

In some embodiments, the amino acid sequence of the enzyme has a maximum of one, two, three, four, five, six, seven, eight, nine or ten amino acid substitutions compared to any one amino acid sequence selected from SEQ ID NO: 2, SEQ ID NO: 3, SEQ ID NO: 5, SEQ ID NO: 7, SEQ ID NO: 8, or any functional fragment thereof.

In some embodiments, the enzyme comprises the amino acid sequence identified by any one of SEQ ID NO: 2, SEQ ID NO: 3, SEQ ID NO: 5, SEQ ID NO: 7, or SEQ ID NO: 8, or any functional fragment thereof.

In some embodiments the compositions, media and methods according to the invention comprise any one or more further enzyme. In some embodiments the one or more further enzyme is selected from list consisting of acetolactate reductoisomerases, acetolactate isomerases, amylase, glucoamylase, hemicellulase, cellulase, glucanase, pullulanase, isoamylase, endo-glucanase and related beta-glucan hydrolytic accessory enzymes, xylanase, xylanase accessory enzymes (for example, arabinofuranosidase, ferulic acid esterase, xylan acetyl esterase) and protease.

In some embodiments the compositions, media and methods according to the invention comprise an enzyme exhibiting ALDC activity, wherein the activity of said ALDC enzyme is in the range of 950 to 2500 Units per mg of protein. In some embodiments the compositions, media and methods according to the invention comprise an enzyme exhibiting ALDC activity, wherein the activity of said ALDC enzyme is in the range of 1000 to 2500 Units per mg of protein. In some embodiments the compositions, media and methods according to the invention comprise an enzyme exhibiting ALDC activity, wherein the activity of said ALDC enzyme is in the range of 1500 to 2500 Units per mg of protein. In some embodiments, the enzyme exhibiting ALDC activity is an enzyme comprising an amino acid sequence having at least 80% identity with any one selected from SEQ ID NO: 2, SEQ ID NO: 3, SEQ ID NO: 5, SEQ ID NO: 7, SEQ ID NO: 8, or any functional fragment thereof. In some embodiments, the enzyme exhibiting ALDC activity is encoded by a nucleic acid sequence having at least 80% identity with SEQ ID NO: 1, SEQ ID NO: 4, SEQ ID NO: 6 or any functional fragment thereof.

Metal Ions

In one aspect, the invention provides methods and compositions comprising ALDC enzymes having a better stability and/or activity. In another aspect the invention provides methods and compositions comprising ALDC enzymes which can be recovered from microorganisms in improved yields.

Surprisingly, it has been found by the present inventors that treatment of ALDC compositions with certain metal ions at certain concentrations provides ALDC enzymes having a better stability and/or activity, and, optionally, the yield of ALDC activity which can be recovered from microorganisms is improved.

In some embodiments, the atomic radius for the metal ion is about 140 pm to about 255 pm. In some embodiments, the atomic radius for the metal ion is about 140 pm to about 165 pm. In some embodiments, the atomic radius for the metal ion is about 140 pm to about 150 pm. In some embodiments, the atomic radius for the metal ion is about 142 pm to about 146 pm.

In some embodiments, the metal ion is selected from the group consisting of $Zn^{2+}$, $Mg^{2+}$, $Mn^{2+}$, $Co^{2+}$, $Cu^{2+}$, $Ba^{2+}$, $Ca^{2+}$ and $Fe^{2+}$ and combinations thereof. In some embodiments, the metal ion is selected from the group consisting of $Zn^{2+}$, $Cu^{2+}$, and $Fe^{2+}$. In some embodiments, the metal ion is selected from the group consisting of $Zn^{2+}$, $Mn^{2+}$, and $Co^{2+}$. In some embodiments, the metal ion is $Zn^{2+}$ or $Mn^{2+}$. In some embodiments, the metal ion is $Zn^{2+}$. The term "zinc" as used herein may be interchangeable with the term "$Zn^{2+}$". The term "metal" as used herein may be interchangeable with the term "metal ion". The term "metal" as used herein may refer to compounds which comprise the metal selected from the group consisting of zinc, magnesium, manganese, cobalt, copper, barium, calcium and iron; compounds which comprise these metals are a source of the respective ions. The term "zinc" as used herein refers to compounds which comprise zinc, such compounds are a source of $Zn^{2+}$ ions. Zinc sulfate ($ZnSO_4$) is example of zinc as referred to herein and is an example of a source of $Zn^{2+}$ ions. Magnesium sulfate ($MgSO_4$) is an example of magnesium as referred to herein and is an example of a source of $Mg^{t+}$ ions. Manganese(II) sulfate ($MnSO_4$) is an example of manganese as referred to herein and is an example of a source of $Mn^{2+}$ ions. Cobalt(II)chloride ($CoCl_2$) is an example of cobalt as referred to herein and is an example of a source of $Co^{2+}$ ions. Copper(II) sulphate ($CuSO_4$) is an example of copper as referred to herein and is an example of a source of $Cu^{2+}$ ions. Barium sulfate ($BaSO_4$) is an example of barium as referred to herein and is an example of a source of $Ba^{t+}$ ions. Calcium sulfate ($CaSO_4$) is an example of calcium as referred to herein and is example of a source of $Ca^{t+}$ ions. Iron(II) sulfate ($FeSO_4$) is an example of iron as referred to herein and is example of a source of $Fe^{2+}$ ions.

The present inventors have found that metal ions such as $Zn^{2+}$, $Mn^{2+}$, $Co^{2+}$, $Cu^{2+}$, and $Fe^{2+}$ increase the stability of ALDC enzyme in different formulations (see Examples), and also improve the recovery yields from microorganisms when the metal ions are used during the production of the enzyme in the cultivation media. Thus, in some embodiments, the present invention provides methods and compositions that increase the recovery yields, stability and/or activity of ALDC enzymes that can be then used, e.g., to produce fermented products such as in brewing.

In one aspect, the present disclosure provides compositions comprising an ALDC enzyme with increased stability and/or activity.

In some embodiments, the ALDC enzyme has an specific activity of at least about 900 units per mg of protein (U/mg), at least about 1000 U/mg, at least about 1500 U/mg, at least about 2000 U/mg, at least about 3000 U/mg at least about 5000 U/mg, at least about 6000 U/mg, at least about 7000 U/mg, at least about 8000 U/mg, at least about 8500 U/mg, at least about 9000 U/mg, at least about 9500 U/mg, or at least about 10000 U/mg as measured by the assays described herein or any suitable assay known in the art. In some embodiments, the ALDC enzyme has an ALDC activity in the range of about 950 to 2500 units per mg of protein (U/mg), about 1000 to 2500 U/mg, or about 1500 to 2500 U/mg as measured by the assays described herein or any suitable assay known in the art. In some embodiments, the ALDC compositions according to the invention comprise an ALDC enzyme with ALDC activity of at least about 900 units per gram of product, at least about 1000 U/g, at least about 1500 U/g, at least about 2000 U/g, at least about 3000 U/g at least about 5000 U/g, such as at least about 6000 U/g, such as at least about 7000 U/g, such as at least about 8000 U/g, such as at least about 8500 U/g, such as at least about 9000 U/g, such as at least about 9500 U/g, such as at least about 10000 U/g as measured by in the assays described herein or any suitable assay known in the art. In some embodiments, a different ALDC activity is used, e.g., depending on the acetolactate content and conditions requirements, e.g. for brewing. In some embodiments, the ALDC compositions according to the invention comprise an ALDC enzyme with ALDC activity of at least about 8000 U/g.

In some embodiments, the compositions comprise an ALDC enzyme and a metal ion, where the metal ion is present at a concentration of about 0.1 μM to about 200 mM, such as about 1 μM to about 200 mM, or about 1 μM to about 500 μM, or about 1 μM to about 300 μM, or about 6 μM to about 300 μM, or about 10 μM to about 100 μM, or about 15 μM to about 50 μM, or about 1 μM to about 150 mM, or about 10 μM to about 150 mM, or about 20 μM to about 120 mM, or about 25 μM to about 100 mM, or about 25 μM to about 50 mM, or about 25 μM to about 20 mM, or about 25 μM to about 50 μM, or about 100 μM to about 20 mM, or about 250 μM to about 20 mM, or about 1 mM to about 20 mM, or about 1 mM to about 5 mM. In some embodiments, the compositions comprise an ALDC enzyme and a metal ion, where the metal ion is present at a concentration of about 1 μM to about 300 μM, such as about 6 μM to about 300 μM, or about 6 μM to about 50 μM, or about 6 μM to about 25 μM. In some embodiments, the compositions comprise an ALDC enzyme and a metal ion, where the metal ion is present at a concentration of about 60 μM to about 150 μM, or about 25 μM to about 150 μM. In some embodiments, the compositions comprise an ALDC enzyme and a metal ion, where the metal ion is present at a concentration of about 100 μM to about 200 mM. In some embodiments, the compositions comprise an ALDC enzyme and a metal ion, where the metal ion is present at a concentration of about 100 μM to about 20 mM. In some embodiments, the compositions comprise an ALDC enzyme and a metal ion, where the metal ion is present at a concentration of about 1 mM to about 5 mM. In some embodiments, the metal ion is selected from the group consisting of $Zn^{2+}$, $Mg^{2+}$, $Mn^{2+}$, $Co^{2+}$, $Cu^{2+}$, $Ba^{2+}$, $Ca^{2+}$ and $Fe^{2+}$ and combinations thereof. In some embodiments, the metal ion is selected from the group consisting of $Zn^{2+}$, $Cu^{2+}$, and $Fe^{2+}$. In some embodiments, the metal ion is selected from the group consisting of $Zn^{2+}$, $Mn^{2+}$, and $Co^{2+}$. In some embodiments, the metal ion is $Zn^{2+}$ or $Mn^{2+}$. In some embodiments, the metal ion is $Zn^{2+}$.

In some embodiments, the compositions comprise an ALDC enzyme and zinc where the zinc is present at a concentration of about 1 μM to about 200 mM, such as about 1 μM to about 500 μM, or about 1 μM to about 300 μM, or about 6 μM to about 300 μM, or about 10 μM to about 100 μM, or about 15 μM to about 50 μM, or about 10 μM to about 150 mM, or about 20 μM to about 120 mM, or about 25 μM to about 100 mM, or about 25 μM to about 50 mM, or about 25 μM to about 20 mM, or about 25 μM to about 50 μM, or about 100 μM to about 20 mM, or about 250 μM to about 20 mM, or about 500 μM to about 20 mM, or about 1 mM to about 20 mM, or about 1 mM to about 10 mM, or about 1 mM to about 5 mM, or about 5 mM to about 20 mM, or about 5 mM to about 10 mM. In some embodiments, the compositions comprise an ALDC enzyme and zinc, where the zinc is present at a concentration of about 1 μM to about 300 μM, such about 6 μM to about 300 μM, or about 6 μM to about 25 μM. In some embodiments, the compositions comprise an ALDC enzyme and zinc, where the zinc is present at a concentration of about 25 μM to about 150 μM or about 60 μM to about 150 μM. In some embodiments, the compositions comprise an ALDC enzyme and zinc, where the zinc is present at a concentration of about 100 μM to about 20 mM. In some embodiments, the compositions comprise an ALDC enzyme and zinc, where the zinc is present at a concentration of about 100 μM to about 10 mM. In some embodiments, the compositions comprise an ALDC enzyme and zinc, where the zinc is present at a concentration of about 1 mM to about 5 mM.

In some embodiments, the compositions comprise an ALDC enzyme and zinc where the zinc is present at a concentration of about 1 mM to about 3 mM, or about 0.75 mM to about 4 mM, or about 0.5 mM to about 5 mM, or about 0.25 mM to about 7.5 mM, or about 0.1 mM to about 10 mM. In some embodiments, the activity of said ALDC enzyme is in the range of 950 to 2500 Units per mg of protein, or 1000 to 2500 Units per mg of protein, or 1500 to 2500 Units per mg of protein.

In some embodiments, the compositions comprise an ALDC enzyme and zinc, where the molar ratio of zinc to enzyme is higher than 1 such as 2:1, or 3:1, or 5:1, or 10:1, or 20:1 or 30:1, or 50:1, or 60:1, or 100:1, or 150:1, or 200:1, or 250:1, or 500:1. In some embodiments, the compositions comprise an ALDC enzyme and zinc, where the molar ratio of zinc to enzyme is 2:1 or higher. In some embodiments, the compositions comprise an ALDC enzyme and zinc, where the molar ratio of zinc to enzyme is 5:1 or higher. In some embodiments, the compositions comprise an ALDC enzyme and zinc, where the molar ratio of zinc to enzyme is 10:1 or higher. In some embodiments, the compositions comprise an ALDC enzyme and zinc, where the molar ratio of zinc to enzyme is 20:1 or higher. In some embodiments, the compositions comprise an ALDC enzyme and zinc, where the molar ratio of zinc to enzyme is 30:1 or higher. In some embodiments, the compositions comprise an ALDC enzyme and zinc, where the molar ratio of zinc to enzyme is 60:1 or higher. The molar concentration of, for example, $Zn^{2+}$, $Mn^{2+}$, $Co^{2+}$ or other metal ions in solution may be determined by inductively coupled plasma optical emission spectrometry (ICP-OES) or similar techniques. The molar concentration of the ALDC enzyme may be determined using Criterion SDS-PAGE. system (such as described in the examples) and the amino acid sequence.

In some embodiments, the ALDC enzyme is an ALDC derivative. In some embodiments, the ALDC derivative is an ALDC enzyme treated with glutaraldehyde. In some embodiments, the ALDC enzyme is treated with glutaraldehyde at a concentration corresponding to about 0.1 to about 5 g of glutaraldehyde per g of pure ALDC enzyme.

In some embodiments, the activity of the ALDC enzyme is in the range of 950 to 2500 Units per mg of protein. In some embodiments, the activity of said ALDC enzyme is in the range of 1000 to 2500 Units per mg of protein. In some embodiments, the activity of said ALDC enzyme is in the range of 1500 to 2500 Units per mg of protein. Thus, in some embodiments, the compositions comprise an ALDC enzyme, where the ALDC enzyme is in the range of 950 to 2500 Units per mg of protein or 1000 to 2500 Units per mg of protein or 1500 to 2500 Units per mg of protein.

In some embodiments, the compositions comprise an ALDC enzyme and zinc, where the zinc is present at a concentration of about 100 μM to about 20 mM, and the activity of said ALDC enzyme is in the range of 1000 to 2500 Units per mg of protein. In some embodiments, the compositions comprise an ALDC enzyme or an ALDC derivative and zinc, where the zinc is present at a concentration of about 250 μM to about 20 mM, and the activity of said ALDC enzyme is in the range of 1000 to 2500 Units per mg of protein.

In some embodiments, the ALDC enzyme compositions further comprise at least one additional enzyme or enzyme derivative selected from the group consisting of acetolactate reductoisomerases, acetolactate isomerases, amylase, glucoamylase, hemicellulase, cellulase, glucanase, pullulanase, isoamylase, endo-glucanase and related beta-glucan hydrolytic accessory enzymes, xylanase, xylanase accessory enzymes (for example, arabinofuranosidase, ferulic acid esterase, and xylan acetyl esterase) and protease.

In some embodiments, the ALDC enzyme compositions described herein are used during fermentation and/or maturation of a beverage preparation process, e.g., beer and wine, to reduce diacetyl levels. The terms "ALDC enzyme composition", "composition comprising an ALDC enzyme" and "composition comprising ALDC" as used herein refer to compositions comprising the ALDC enzyme. The composition may be in the form of a solution. As used herein, the terms "ALDC enzyme composition" and "compositions comprising ALDC" are mutually exclusive with media (such as cultivation media, fermentation media or maturation media) which comprise microorganisms expressing ALDC and/or capable of expressing ALDC when cultured under conditions permitting expression of the enzyme. Examples of ALDC enzyme compositions and compositions comprising ALDC include compositions comprising ALDC in a purified form. ALDC may be purified from a media comprising microorganisms capable of expressing ALDC wherein said media has been cultured under conditions permitting expression of ALDC. The term "purified" means that ALDC is present at a high level. Preferably, ALDC is the predominant component present in the composition. Preferably, ALDC is present at a level of at least about 90%, or at least about 95% or at least about 98%, said level being determined on a dry weight/dry weight basis with respect to the total composition under consideration. In some embodiments, an ALDC enzyme composition further comprises a metal ion such as zinc.

As used herein, the terms "beverage" and "beverage(s) product" include such foam forming fermented beverages as beer brewed with 100% malt, beer brewed under different types of regulations, ale, dry beer, near beer, light beer, low alcohol beer, low calorie beer, porter, bock beer, stout, malt liquor, non-alcoholic beer, non-alcoholic malt liquor and the like. The term "beverages" or "beverages product" also includes non-foaming beer and alternative malt beverages such as fruit flavored malt beverages, e. g., citrus flavored, such as lemon-, orange-, lime-, or berry-flavored malt beverages, liquor flavored malt beverages, e. g., vodka-, rum-, or tequila-flavored malt liquor, or coffee flavored malt beverages, such as caffeine-flavored malt liquor, and the like. The term "beverages" or "beverages product" also includes beer made with alternative materials other than malted barley, such as rye, corn, oats, rice, millet, triticale, cassava, sorghum, barley, wheat and a combination thereof. The term "beverages" or "beverages product" also includes other fermented products such as wine or ciders or perry or sake.

Beer is traditionally referred to as an alcoholic beverage derived from malt, such as malt derived from barley grain, and optionally adjunct, such as starch containing plant material (e.g. cereal grains) and optionally flavored, e.g. with hops. In the context of the present invention, the term "beer" includes any fermented wort, produced by fermentation/brewing of a starch-containing plant material, thus in particular also beer produced exclusively from adjunct, or any combination of malt and adjunct. Beer can be made from a variety of starch-containing plant material by essentially the same process, where the starch consists mainly of glucose homopolymers in which the glucose residues are linked by alpha-1, 4- or alpha-1,6-bonds, with the former predominating. Beer can be made from alternative materials such as rye, corn, oats, rice, millet, triticale, cassava, sorghum, wheat, barley and a combination thereof.

In some embodiments, the invention provides a fermentation media (e.g. beer and/or wine and/or cider and/or perry and/or sake fermentation) comprising an ALDC enzyme and metal ion at a concentration of about 0.1 μM to about 200 mM, or about 1 μM to about 200 mM, such as about 1 μM to about 500 μM, or about 0.1 μM to about 300 μM, or about 1 μM to about 300 μM, or about 6 μM to about 300 μM, or about 1 μM to about 100 μM, or about 1 μM to about 50 μM, or about 6 μM to about 50 μM, or about 6 μM to about 25 μM. In some embodiments, the invention provides a fermentation media (e.g. beer and/or wine and/or cider and/or perry and/or sake fermentation) comprising an ALDC enzyme and metal ion at a concentration of about 0.1 μM to about 100 mM, such as about 0.1 μM to about 10 μM, or 1 μM to about 100 mM, or 1 μM to about 10 μM, or 6 μM to about 10 μM, or about 10 μM to about 200 μM, or about 50 μM to about 1 mM, or about 100 μM to about 10 mM, or about 100 μM to about 50 mM, or about 100 μM to about 100 mM, or about 100 μM to about 200 mM, or about 250 μM to about 120 mM, or about 500 μM to about 100 mM, or about 1 mM to about 50 mM, or about 1 mM to about 20 mM, or about 1 mM to about 5 mM. In some embodiments, the invention provides a fermentation media (e.g. beer and/or wine and/or cider and/or perry and/or sake fermentation) comprising an ALDC enzyme and metal ion at a concentration of about 0.1 μM to about 200 mM or about 1 μM to about 200 mM, such as about 1 μM to about 500 μM, or about 1 μM to about 300 μM, or about 6 μM to about 300 μM, or about 1 μM to about 100 μM, or about 1 μM to about 50 μM, or about 6 μM to about 50 μM, or about 6 μM to about 25 μM. In some embodiments, the invention provides a fermentation media (e.g. beer and/or wine and/or cider and/or perry and/or sake fermentation) comprising an ALDC enzyme and metal ion at a concentration of about 1 μM to about 300 μM, or about 6 μM to about 300 μM, or about 1 μM to about 100 μM, or about 1 μM to about 50 μM, or about 6 μM to about 50 μM or about 6 μM to about 25 μM. In some embodiments, the metal ion is selected from the group consisting of $Zn^{2+}$, $Mg^{2+}$, $Mn^{2+}$, $Co^{2+}$, $Cu^{2+}$, $Ba^{2+}$, $Ca^{2+}$ and $Fe^{2+}$ and combinations thereof. In some embodiments, the metal ion is selected from the group consisting of $Zn^{2+}$, $Cu^{2+}$, and $Fe^{2+}$. In some embodiments, the metal ion is selected from the group consisting of $Zn^{2+}$, $Mn^{2+}$, and $Co^{2+}$. In some embodiments, the metal ion is $Zn^{2+}$ or $Mn^{2+}$. In some embodiments, the metal ion is $Zn^{2+}$. In some embodiments, the activity of said ALDC enzyme is in the range of 950 to 2500 Units per mg of protein, or 1000 to 2500 Units per mg of protein, or 1500 to 2500 Units per mg of protein. In some embodiments, the fermentation media (e.g. beer and/or wine and/or cider and/or perry and/or sake fermentation) further comprises at least one additional enzyme or enzyme derivative selected from the group consisting of acetolactate reductoisomerases, acetolactate isomerases, amylase, glucoamylase, hemicellulase, cellulase, glucanase, pullulanase, isoamylase, endo-glucanase and related beta-glucan hydrolytic accessory enzymes, xylanase, xylanase accessory enzymes (for example, arabinofuranosidase, ferulic acid esterase, and xylan acetyl esterase) and protease.

In some embodiments, the invention provides a maturation media (e.g. beer and/or wine and/or cider and/or perry and/or sake fermentation) comprising an ALDC enzyme and metal ion at a concentration of about 0.1 μM to about 200 mM, or 1 μM to about 200 mM, such as about 1 μM to about 500 μM, or about 0.1 μM to about 300 μM, or about 1 μM to about 300 μM, or about 6 μM to about 300 μM, or about 1 μM to about 100 μM, or about 1 μM to about 50 μM, or about 6 μM to about 50 μM, or about 6 μM to about 25 μM. In some embodiments, the invention provides a maturation media (e.g. beer and/or wine and/or cider and/or perry and/or sake fermentation) comprising an ALDC enzyme and metal ion at a concentration of about 0.1 μM to about 100 mM, or 1 μM to about 100 mM, such as about 0.1 μM to about 10 μM, or 1 μM to about 10 μM, or 6 μM to about 10 μM, or about 10 μM to about 200 μM, or about 50 μM to about 1 mM, or about 100 μM to about 10 mM, or about 100 μM to about 50 mM, or about 100 μM to about 100 mM, or about 100 μM to about 200 mM, or about 250 μM to about 120 mM, or about 500 μM to about 100 mM, or about 1 mM to about 50 mM, or about 1 mM to about 20 mM, or about 1 mM to about 5 mM. In some embodiments, the invention provides a maturation media (e.g. beer and/or wine and/or cider and/or perry and/or sake fermentation) comprising an ALDC enzyme and metal ion at a concentration of about 1 μM to about 500 μM, or about 1 μM to about 300 μM, or about 6 μM to about 300 μM, or about 1 μM to about 100 μM, or about 1 μM to about 50 μM, or about 6 μM to about 50 μM, or about 6 μM to about 25 μM. In some embodiments, the invention provides a maturation media (e.g. beer and/or wine and/or cider and/or perry and/or sake fermentation) comprising an ALDC enzyme and metal ion at a concentration of about 1 μM to about 300 μM, or about 6 μM to about 300 μM, or about 1 μM to about 100 μM, or about 1 μM to about 50 μM, or about 6 μM to about 50 μM, or about 6 μM to about 25 μM. In some embodiments, the metal ion is selected from the group consisting of $Zn^{2+}$, $Mg^{2+}$, $Mn^{2+}$, $Co^{2+}$, $Cu^{2+}$, $Ba^{2+}$, $Ca^{2+}$ and $Fe^{2+}$ and combinations thereof. In some embodiments, the metal ion is selected from the group consisting of $Zn^{2+}$, $Cu^{2+}$, and $Fe^{2+}$. In some embodiments, the metal ion is selected from the group consisting of $Zn^{2+}$, $Mn^{2+}$, and $Co^{2+}$. In some embodiments, the metal ion is $Zn^{2+}$ or $Mn^{2+}$. In some embodiments, the metal ion is $Zn^{2+}$. In some embodiments, the activity of said ALDC enzyme is in the range of 950 to 2500 Units per mg of protein, or 1000 to 2500 Units per mg of protein, or 1500 to 2500 Units per mg of protein. In some embodiments, the maturation media (e.g. beer and/or wine maturation) further comprises at least one additional enzyme or enzyme derivative selected from the group consisting of acetolactate reductoisomerases, acetolactate isomerases, amylase, glucoamylase, hemicellulase, cellulase, glucanase, pullulanase, isoamylase, endo-glucanase and related beta-glucan hydrolytic accessory enzymes, xylanase, xylanase accessory enzymes (for example, arabinofuranosidase, ferulic acid esterase, and xylan acetyl esterase) and protease.

In some embodiments, metal ions such as $Zn^{2+}$, $Mg^{2+}$, $Mn^{2+}$, $Co^{2+}$, $Cu^{2+}$, $Ba^{2+}$, $Ca^{2+}$ and $Fe^{2+}$ and combinations thereof are added to the cultivation and/or fermentation media during and/or after ALDC production to increase the recovered yields from microorganisms.

The term "cultivation media" as used herein refers to a media which supports the growth of microorganisms such as an ALDC producing host cell. Examples of a cultivation media include: media based on MOPs buffer with, for instance, urea as the major nitrogen source and maltrin as the main carbon source; and TSB broth. In some embodiments, the invention provides a cultivation media for an ALDC producing host cell comprising a metal ion at a concentration of about 1 μM to about 1 mM. In some embodiments, the invention provides a cultivation media for an ALDC producing host cell comprising a metal ion at a concentration of about 25 μM to about 150 μM. In some embodiments, the invention provides a cultivation media for an ALDC producing host cell comprising a metal ion at a concentration of about 25 μM to about 50 μM. In some embodiments, the invention provides a cultivation media for an ALDC producing host cell comprising a metal ion at a concentration of about 30 μM to about 40 μM. In some embodiments, the invention provides a cultivation media for an ALDC producing host cell comprising a metal ion at a concentration of about 40 μM to about 150 μM. In some embodiments, the invention provides a cultivation media for an ALDC producing host cell comprising a metal ion at a concentration of about 60 μM to about 150 μM. In some embodiments, the metal ion is selected from the group consisting of $Zn^{2+}$, $Mg^{2+}$, $Mn^{2+}$, $Co^{2+}$, $Cu^{2+}$, $Ba^{2+}$, $Ca^{2+}$ and $Fe^{2+}$ and combinations thereof. In some embodiments, the metal ion is selected from the group consisting of $Zn^{2+}$, $Cu^{2+}$, and $Fe^{2+}$. In some embodiments, the metal ion is selected from the group consisting of $Zn^{2+}$, $Mn^{2+}$, and $Co^{2+}$. In some embodiments, the metal ion is $Zn^{2+}$ or $Mn^{2+}$. In some embodiments, the metal ion is $Zn^{2+}$. In some embodiments, the activity of said ALDC enzyme is in the range of 950 to 2500 Units per mg of protein, or 1000 to 2500 Units per mg of protein, or 1500 to 2500 Units per mg of protein.

Materials may be added to an enzyme-containing composition to improve the properties of the composition. Non-limiting examples of such additives include: salts (e.g., alkali salts, earth metal salts, additional chloride salts, sulfate salts, nitrate salts, carbonate salts, where exemplary counter ions are calcium, potassium, and sodium), inorganic minerals or clays (e.g., zeolites, kaolin, bentonite, talcs and/or silicates), carbohydrates (e.g., sucrose and/or starch), coloring pigments (e.g., titanium dioxide), biocides (e.g., Rodalon®, Proxel®), dispersants, anti-foaming agents, reducing agents, acid agents, alkaline agents, enzyme stabilizers (e.g. polyol such as glycerol, propylene glycol, sorbitol, inorganic salts, sugars, sugar or a sugar alcohol, lactic acid, boric acid, or a boric acid derivative and combinations thereof), enzyme inhibitors, preservative (e.g. methyl paraben, propyl paraben, benzoate, sorbate or other food approved preservatives) and combinations thereof. Excipients which may be used in the composition, or the preparation thereof, include maltose, maltose syrup, sucrose, glucose (including glucose syrup or dried glucose syrup), pre-cooked starch, gelatinised starch, L-lactic, ascorbyl palmitate, tocopherols, lecithins, citric acid, citrates, phosphoric, phosphates, sodium alginate, carrageenan, locust bean gum, guar gum, xanthan gum, pectins, sodium carboxymethylcellulose, mono- and diglycerides, citric acid esters of mono- and diglycerides, sucrose esters, carbon dioxide, argon, helium, nitrogen, nitrous oxide, oxygen, hydrogen, and starch sodium octenylsuccinate.

Methods

In some aspects the invention provides methods to improve stability and/or activity of ALDC enzymes. In some aspects the invention provides methods to improve ALDC recovery from microorganisms.

In some embodiments, the invention provides methods for increasing the activity and/or stability of an ALDC enzyme in a composition comprising ALDC wherein said method comprises the step of adding a metal ion to the composition so that said metal ion is present in said composition at a concentration of about 1 μM to about 200 mM, such as about 1 μM to about 500 μM, or about 1 μM to about 300 μM, or about 6 μM to about 300 μM, or about 1 μM to about 100 μM, or about 1 μM to about 50 μM, or about 10 μM to about 150 mM, or about 20 μM to about 120 mM, or about 25 μM to about 100 mM, or about 25 μM to about 50 mM, or about 25 μM to about 20 mM, or about 25 μM to about 50 μM, or about 100 μM to about 20 mM, or about 250 μM to about 20 mM, or about 500 μM to about 20 mM, or about 1 mM to about 20 mM, or about 1 mM to about 10 mM, or about 1 mM to about 5 mM, or about 5 mM to about 20 mM, or about 5 mM to about 10 mM. In some embodiments, the invention provides methods for increasing the activity and/or stability of an ALDC enzyme in a cultivation media comprising an ALDC producing host cell wherein said method comprises the step of adding a metal ion to the media so that said metal ion is present in said media at a concentration of about 1 μM to about 1 mM, such as about 1 μM to about 300 μM, about 6 μM to about 300 μM, about 25 μM to about 150 μM, or about 60 μM to about 150 μM. In some embodiments, the invention provides methods for increasing the activity and/or stability of an ALDC enzyme in a fermentation and/or maturation media comprising an ALDC enzyme wherein said method comprises the step of adding a metal ion to the media so that said metal ion is present in said media at a concentration of about 1 μM to about 300 μM, such as about 6 μM to about 300 μM, about 1 μM to about 100 μM, about 1 μM to about 50 μM, about 1 μM to about 25 μM, or about 6 μM to about 25 μM. In some embodiments, the invention provides methods for increasing the activity and/or stability of an ALDC enzyme comprising adding a metal ion at a concentration of about 25 μM to about 150 μM in a media. In some embodiments, the invention provides methods for increasing the activity and/or stability of an ALDC enzyme comprising adding a metal ion at a concentration of about 100 μM to about 20 mM. In some embodiments, the invention provides methods for increasing the activity and/or stability of an ALDC enzyme comprising adding a metal ion at a concentration of about 1 mM to about 5 mM. In some embodiments, the metal ion is selected from the group consisting of $Zn^{2+}$, $Mg^{2+}$, $Mn^{2+}$, $Co^{2+}$, $Cu^{2+}$, $Ba^{2+}$, $Ca^{2+}$ and $Fe^{2+}$ and combinations thereof.

In some embodiments, the metal ion is selected from the group consisting of $Zn^{2+}$, $Cu^{2+}$, and $Fe^{2+}$. In some embodiments, the metal ion is selected from the group consisting of $Zn^{2+}$, $Mn^{2+}$, and $Co^{2+}$. In some embodiments, the metal ion is $Zn^{2+}$ or $Mn^{2+}$. In some embodiments, the metal ion is $Zn^{2+}$.

In some embodiments, the invention provides methods for increasing the activity and/or stability of an ALDC enzyme in a composition comprising ALDC wherein said method comprises the step of adding a zinc to the composition so that said zinc is present in said composition at a concentration of about 1 μM to about 200 mM, such as about 1 μM to about 500 μM, or about 1 μM to about 300 μM, or about 6 μM to about 300 μM, or about 1 μM to about 100 μM, or about 1 μM to about 50 μM, or about 10 μM to about 150 mM, or about 20 μM to about 120 mM, or about 25 μM to about 100 mM, or about 25 μM to about 50 mM, or about 25 μM to about 20 mM, or about 25 μM to about 50 μM, or about 100 μM to about 20 mM, or about 250 μM to about 20 mM, or about 500 μM to about 20 mM, or about 1 mM to about 20 mM, or about 1 mM to about 10 mM, or about 1 mM to about 5 mM, or about 5 mM to about 20 mM, or about 5 mM to about 10 mM. In some embodiments, the invention provides methods for increasing the activity and/or stability of an ALDC enzyme in a cultivation media comprising an ALDC producing host cell wherein said method comprises the step of adding a zinc at a concentration of about 1 μM to about 1 mM, such as about 1 μM to about 300 μM, about 6 μM to about 300 μM, about 25 μM to about 150 μM, or about 60 μM to about 150 μM. In some embodiments, the invention provides methods for increasing the activity and/or stability of an ALDC enzyme in a fermentation and/or maturation media comprising an ALDC enzyme wherein said method comprises the step of adding a zinc to the media so that said zinc is present in said media at a concentration of about 1 μM to about 300 μM, such as about 6 μM to about 300 μM, about 1 μM to about 100 μM, about 1 μM to about 50 μM, about 1 μM to about 25 μM, or about 6 μM to about 25 μM. In some embodiments, methods for increasing the activity and/or stability of an ALDC enzyme comprise adding a zinc to a media so that the zinc is at a concentration of about 25 μM to about 150 μM in the media. In some embodiments, methods for increasing the activity and/or stability of an ALDC enzyme comprise adding a zinc at a concentration of about 100 μM to about 20 mM. In some embodiments, methods for increasing the activity and/or stability of an ALDC enzyme comprise adding a zinc at a concentration of about 1 mM to about 5 mM. In some embodiments, methods for increasing the activity and/or stability of an ALDC enzyme comprise adding zinc at a molar ratio of zinc to ALDC enzyme that is higher than 1 such as 2:1, or 3:1, or 5:1, or 10:1, or 20:1 or 30:1, or 50:1, or 60:1, or 100:1, or 150:1, or 200:1 or 250:1 in said composition. In some embodiments, methods for increasing the activity and/or stability of an ALDC enzyme comprise adding zinc at a molar ratio of zinc to ALDC enzyme of 5:1 or higher in said composition. In some embodiments, methods for increasing the activity and/or stability of an ALDC enzyme comprise adding zinc at a molar ratio of zinc to ALDC enzyme of 10:1 or higher in said composition. In some embodiments, methods for increasing the activity and/or stability of an ALDC enzyme comprise adding zinc at a molar ratio of zinc to ALDC enzyme of 20:1 or higher in said composition. In some embodiments, methods for increasing the activity and/or stability of an ALDC enzyme comprise adding zinc at a molar ratio of zinc to ALDC enzyme of 30:1 or higher in said composition.

In some embodiments, the metal ion is added (e.g. as a supplement) to a cultivation media during the production of said ALDC enzyme by an ALDC producing host cell. In some embodiments, the metal ion is added at a concentration of about 0.1 μM to about 1 mM, such as about 25 μM to about 150 μM, or about 40 μM to about 150 μM, or about 60 μM to about 150 μM, or about 25 μM to about 50 μM, or 30 μM to about 40 μM. In some embodiments, the metal ion is selected from the group consisting of $Zn^{2+}$, $Mg^{2+}$, $Mn^{2+}$, $Co^{2+}$, $Cu^{2+}$, $Ba^{2+}$, $Ca^{2+}$ and $Fe^{2+}$ and combinations thereof. In some embodiments, the metal ion is selected from the group consisting of $Zn^{2+}$, $Cu^{2+}$, and $Fe^{2+}$. In some embodiments, the metal ion is selected from the group consisting of $Zn^{2+}$, $Mn^{2+}$, and $Co^{2+}$. In some embodiments, the metal ion is $Zn^{2+}$ or $Mn^{2+}$. In some embodiments, the metal ion is $Zn^{2+}$. Thus, in some embodiments zinc is added (e.g. as a supplement) to a cultivation media during the production of said ALDC enzyme by an ALDC producing host cell at a concentration of 1 μM to about 1 mM, such as 25 μM to about 150 μM, or about 40 μM to about 150 μM, or 60 μM to about 150 μM.

In some embodiments, the host cell is a *Bacillus* host cell. In some embodiments, *Bacillus* host cell is *Bacillus subtilis*.

In some embodiments, the metal ion is added in the fermentation media during production of a fermented beverage. In some embodiments, the metal ion is added in the fermentation media during beer and/or wine and/or cider and/or perry and/or sake fermentation. In some embodiments, the metal ion is selected from the group consisting of $Zn^{2+}$, $Mg^{2+}$, $Mn^{2+}$, $Co^{2+}$, $Cu^{2+}$, $Ba^{2+}$, $Ca^{2+}$ and $Fe^{2+}$ and combinations thereof. In some embodiments, the metal ion is selected from the group consisting of $Zn^{2+}$, $Cu^{2+}$, and $Fe^{2+}$. In some embodiments, the metal ion is selected from the group consisting of $Zn^{2+}$, $Mn^{2+}$, and $Co^{2+}$. In some embodiments, the metal ion is $Zn^{2+}$ or $Mn^{2+}$. In some embodiments, the metal ion is $Zn^{2+}$. Thus, in some embodiments, zinc is added in a fermentation media during beer and/or wine and/or cider and/or perry and/or sake fermentation. In some embodiments, zinc is added at a concentration of about 1 μM to about 1 mM, such as about 1 μM to about 300 μM, or about 6 μM to about 300 μM, or about 1 μM to about 100 μM, or 25 μM to about 50 μM, or 30 μM to about 40 μM, or 1 μM to about 50 μM, or 6 μM to about 50 μM, or 1 μM to about 25 μM, or 6 μM to about 25 μM. In some embodiments zinc and the ALDC enzyme are added in a composition, wherein zinc is present in said composition at a concentration of 0.1 μM to about 200 mM or 1 μM to about 200 mM, or 0.1 mM to about 120 mM, such as 1 mM to about 20 mM, or 1 mM to about 10 mM, or 1 mM to 5 mM. In some embodiments zinc and the ALDC enzyme are added in a composition, wherein the molar ratio of zinc to ALDC enzyme in the composition is higher than 1 such as 2:1, or 3:1, or 5:1, or 10:1, or 20:1 or 30:1, or 50:1, or 60:1.

In some embodiments, the metal ion is added in the maturation media during production of a fermented beverage. In some embodiments, the metal ion is added the maturation media during beer and/or wine and/or cider and/or perry and/or sake fermentation. In some embodiments, the metal ion is selected from the group consisting of $Zn^{2+}$, $Mg^{2+}$, $Mn^{2+}$, $Co^{2+}$, $Cu^{2+}$, $Ba^{2+}$, $Ca^{2+}$ and $Fe^{2+}$ and combinations thereof. In some embodiments, the metal ion is selected from the group consisting of $Zn^{2+}$, $Cu^{2+}$, and $Fe^{2+}$. In some embodiments, the metal ion is selected from the group consisting of $Zn^{2+}$, $Mn^{2+}$, and $Co^{2+}$. In some embodiments, the metal ion is $Zn^{2+}$ or $Mn^{2+}$. In some embodiments, the metal ion is $Zn^{2+}$. Thus, in some embodiments, zinc is added in a maturation media during beer and/or wine and/or cider and/or perry and/or sake fermentation. In some embodiments, zinc is added at a concentration of 1 μM to about 1 mM, such as 1 μM to about 300 μM, or about 6 μM to about 300 μM, or about 1 μM to about 100 μM, or 25 μM to about 50 μM, or 30 μM to about 40 μM, or 1 μM to about 50 μM, or 6 μM to about 50 μM, or 1 μM to about 25 μM, or 6 μM to about 25 μM. In some embodiments zinc and ALDC are added in a composition, wherein zinc is present in said composition at a concentration of 0.1 μM to about 200 mM, or 1 μM to about 200 mM, or 0.25 mM to about 120 mM, such as 1 mM to about 20 mM, or 1 mM to about 10 mM, or 1 mM to about 5 mM. In some embodiments zinc and the ALDC enzyme are added in a composition, wherein the molar ratio of zinc to ALDC enzyme in the composition is higher than 1 such as 2:1, or 3:1, or 5:1, or 10:1, or 20:1 or 30:1, or 50:1, or 60:1.

In some embodiments, a method of producing acetoin is provided in the disclosure. In some embodiments, a method of decomposing acetolactate is provided in the disclosure. In some embodiments, acetolactate is decomposed to acetoin. The methods involve the step of treating a substrate with an ALDC enzyme and a metal ion, wherein the metal ion is present at a concentration of about 1 μM to about 200 mM, such as about 1 μM to about 500 μM, or about 1 μM to about 300 μM, or about 6 μM to about 300 μM, or about 1 μM to about 100 μM, or about 1 μM to about 50 μM, or 6 μM to about 50 μM, or 6 μM to about 25 μM, or about 10 μM to about 150 mM, or about 20 μM to about 120 mM, or about 25 μM to about 100 mM, or about 25 μM to about 50 mM, or about 25 μM to about 20 mM, or about 25 μM to about 50 μM, or about 100 μM to about 20 mM, or about 250 μM to about 20 mM, or about 1 mM to about 20 mM, or about 1 mM to about 5 mM. In some embodiments the metal ion and the ALDC enzyme are added in a composition, where the metal ion is present in said composition at a concentration of 0.1 μM to about 200 mM, or 1 μM to about 200 mM, or 0.25 mM to about 120 mM, such as 1 mM to about 20 mM, or 1 mM to about 5 mM. In some embodiments the metal ion and the ALDC enzyme are added in a composition, wherein the molar ratio of metal ion to ALDC enzyme in the composition is higher than 1 such as 2:1, or 3:1, or 5:1, or 10:1, or 20:1 or 30:1, or 50:1, or 60:1. In some embodiments, the metal ion is selected from the group consisting of $Zn^{2+}$, $Mg^{2+}$, $Mn^{2+}$, $Co^{2+}$, $Cu^{2+}$, $Ba^{2+}$, $Ca^{2+}$ and $Fe^{2+}$ and combinations thereof. In some embodiments, the metal ion is selected from the group consisting of $Zn^{2+}$, $Cu^{2+}$, and $Fe^{2+}$. In some embodiments, the metal ion is selected from the group consisting of $Zn^{2+}$, $Mn^{2+}$, and $Co^{2+}$. In some embodiments, the metal ion is $Zn^{2+}$ or $Mn^{2+}$. In some embodiments, the metal ion is $Zn^{2+}$. Thus, in some embodiments, the methods involve the step of treating a substrate with an ALDC enzyme and zinc, wherein said zinc is present at a concentration of about 1 μM to about 1 mM, such as 1 μM to about 300 μM, or about 6 μM to about 300 μM, or 1 μM to about 100 μM, or 6 μM to about 100 μM, or 6 μM to about 50 μM, or 6 μM to about 25 μM. In some embodiments zinc and the ALDC enzyme are added in a composition, where zinc is present in said composition at a concentration of 0.1 μM to about 200 mM, or 1 μM to about 200 mM, or 0.25 mM to about 120 mM, such as 1 mM to about 20 mM, or 1 mM to about 5 mM. In some embodiments zinc and the ALDC enzyme are added in a composition, wherein the molar ratio of zinc to ALDC enzyme in the composition is higher than 1 such as 2:1, or 3:1, or 5:1, or 10:1, or 20:1 or 30:1, or 50:1, or 60:1.

In some embodiments a method of producing acetoin during the production of a fermented beverage is provided in the disclosure. In some embodiments, a method of decomposing acetolactate during the production of a fermented beverage is provided in the disclosure. In some embodiments, acetolactate is decomposed to acetoin.

Fermented Products

In one aspect the present invention relates to a process for producing fermented alcoholic products with a low diacetyl content by fermentation of a carbohydrate containing substrate with a microorganism. As used herein, a fermented alcoholic product with "low diacetyl content" refers to a fermented alcoholic product (e.g. a beer and/or a wine and/or a cider and/or a perry and/or sake) produced by fermentation of a carbohydrate containing substrate with a composition comprising ALDC in the presence of a metal ion (such as zinc) wherein the diacetyl levels are lower when compared to the fermented alcoholic produced by fermentation of a carbohydrate containing substrate with a composition comprising ALDC in the absence of a metal ion (such as zinc) under the same fermentation conditions (e.g. same temperature and for the same length of time). Examples of fermented alcoholic products with low diacetyl content are fermented alcoholic products in which the levels of diacetyl are less than about 1 ppm and/or the diacetyl levels are below about 0.5 mg/L. In one embodiment, the diacetyl levels are less than about 0.5 ppm, or less than about 0.1 ppm, or less than about 0.05 ppm, or less than about 0.01 ppm, or less than about 0.001 ppm. In one embodiment, the diacetyl levels are about less than 0.1 mg/L, or about less than 0.05 mg/L, or about less than 0.01 mg/L or about less than 0.001 mg/L.

When carbohydrate containing substrates, such as wort (e.g. worts with low malt content) or fruit juices (such as grape juice, apple juice or pear juice), are fermented with yeast or other microorganisms, various processes take place in addition to the alcohol fermentation which may cause generation of undesired by-products, e.g., the formation of diacetyl which has a strong and unpleasant smell even in very low concentrations. Alcoholic beverages, such as beer or wine or cider or perry or sake, may thus have an unacceptable aroma and flavor if the content of diacetyl considerably exceeds certain limits, e.g., in the case of some beers about 0.1 ppm.

Formation of diacetyl is also disadvantageous in the industrial production of ethanol because it is difficult to separate diacetyl from ethanol by distillation. A particular problem arises in the preparation of absolute ethanol where ethanol is dehydrated by azeotropic distillation with benzene. Diacetyl will accumulate in the benzene phase during the azeotropic distillation which may give rise to mixtures of diacetyl and benzene which makes it difficult to recover the benzene used for the azeotropic distillation.

The conventional brewing of beer comprises fermenting the wort with a suitable species of yeast, such as *Saccharomyces cerevisae* or *Saccharomyces carlsbergensis.*

Typically in conventional brewing, the fermentation is usually effected in two steps, a main fermentation of a duration of normally 5 to 12 days and a secondary fermentation—a so-called maturation process-which may take from up to 12 weeks. During the main fermentation most of the carbohydrates in the wort are converted to ethanol and carbon dioxide. Maturation is usually effected at a low temperature in the presence of a small residual amount of yeast. The purposes of the maturation are, inter alia, to precipitate undesirable, high molecular weight compounds and to convert undesirable compounds to compounds, such as diols, which do not affect flavor and aroma. For example butanediol, the final product of the conversion of α-acetolactate and diacetyl in beer, is typically reported as a compound with neutral sensory characteristics. The term "fermentation media" as used herein refers to a medium comprising carbohydrate containing substrates which can be fermented by yeast or other microorganisms to produce, for example, beer or wine or cider or perry or sake. Examples of fermentation media include: wort, and fruit juices (such as grape juice, apple juice and pear juice). Example 9 details an example of suitable wort. The term "maturation media" as used herein refers to a medium comprising carbohydrate containing substrates which have been fermented by yeast or other microorganisms to produce, for example, beer or wine or cider or perry or sake. Examples of maturation media include partially fermented wort and fruit juices (such as grape juice, apple juice and pear juice). In some embodiments, the invention provides a fermentation or maturation media for an ALDC producing host cell comprising a metal ion at a concentration of about 1 to about 300 μM. In some embodiments, the invention provides a fermentation or maturation media for an ALDC producing host cell comprising a metal ion at a concentration of about 6 μM to about 25 μM.

In some aspects, the present invention relates to the use of a composition as described herein in beer and/or wine and/or cider and/or perry and/or sake fermentation. In some embodiments, the present invention comprises the use of the ALDC compositions described herein to decompose acetolactate during beer and/or wine and/or cider and/or perry and/or sake fermentation or maturation. Also, the invention comprises the use of ALDC derivative according to the invention to decompose acetolactate during beer and/or wine and/or cider and/or perry and/or sake fermentation or maturation.

In some embodiments, the methods of the invention are thus characterized by the treatment of a substrate with a composition comprising ALDC or an ALDC derivative as described herein during or in continuation of a fermentation process, e.g., maturation.

Thus, in some embodiments, acetolactate is enzymatically decarboxylated to acetoin, the result being that when undesirable, the formation of diacetyl from acetolactate is avoided. In some embodiments, other enzymes are used in combination with ALDC for the conversion of α-acetolactate. Examples of such enzymes include, but are not limited to, acetolactate reductoisomerases or isomerases.

In some embodiments, the ALDC and/or ALDC derivative compositions described herein are used together with ordinary yeast in batch fermentation.

Instead of using the enzyme in a free state, it may be used in an immobilized state, the immobilized enzyme being added to the wort during or in continuation of the fermentation (e.g., during maturation). The immobilized enzyme may also be maintained in a column through which the fermenting wort or the beer is passed. The enzyme may be immobilized separately, or coimmobilized yeast cells and acetolactate decarboxylase may be used.

In some embodiments, the ALDC and/or ALDC derivative compositions described herein are used during beer and/or wine and/or cider and/or perry and/or sake fermentation or maturation to reduce the diacetyl levels to below about 1 ppm, or about less than 0.5 ppm, or about less than 0.1 ppm, or about less than 0.05 ppm or about less than 0.01 ppm, or about less than 0.001 ppm. In some embodiments, the ALDC and/or ALDC derivative compositions described herein are used during beer and/or wine and/or cider and/or perry and/or sake fermentation or maturation to reduce the diacetyl levels to below 0.1 ppm.

In some embodiments, the ALDC and/or ALDC derivative compositions described herein are used during beer and/or wine and/or cider and/or perry and/or sake fermentation or maturation to reduce VDK content below 0.1 mg/L, or about less than 0.05 mg/L, or less than 0.01 mg/L or less than 0.001 mg/L. Total VDK refers to the amount of Diacetyl plus 2,3-pentanedione. In some embodiments, the ALDC and/or ALDC derivative compositions described herein are used during beer and/or wine and/or cider and/or perry and/or sake fermentation or maturation to reduce Total VDK content below 0.1 mg/L.

In some embodiments, the ALDC and/or ALDC derivative compositions described herein are used during beer and/or wine and/or cider and/or perry and/or sake fermentation or maturation to reduce the diacetyl levels to below about 0.5 mg/L, or about less than 0.1 mg/L, or about less than 0.05 mg/L, or about less than 0.01 mg/L or about less than 0.001 mg/L. In some embodiments, the ALDC and/or ALDC derivative compositions described herein are used during beer and/or wine and/or cider and/or perry and/or sake fermentation or maturation to reduce the diacetyl levels to below 0.1 mg/L.

In some embodiments, the ALDC and/or ALDC derivative compositions described herein are used during beer and/or wine and/or cider and/or perry and/or sake fermentation or maturation to reduce other vicinal diketones (such as 2,3 pentanedione) to below 0.1 mg/L, or about less than 0.05 mg/L, or less than 0.01 mg/L or less than 0.001 mg/L.

The processes of the invention can not only be used in connection with the brewing of beer, but is also suitable for the production of any suitable alcoholic beverage where a reduction in diacetyl levels or other vicinal diketones is desirable (e.g. wine, sake, cider, perry, etc.). In some embodiments, the processes of the invention can be used in the production of wine where similar advantages are obtained, in particular a reduction in the maturation period and a simplification of the process. Of special interest in this context is the use of acetolactate converting enzymes in connection with the so-called malo-lactic fermentation. This process which is affected by microorganisms as species of *Leuconostoc, Lactobacillus* or *Pediococcus* is carried out after the main fermentation of wine in order to increase the pH of the product as well as its biological stability and to develop the flavor of the wine. Moreover, it is highly desirable to carry out the fermentation since it makes possible rapid bottling and thereby improves the cash-flow of wineries substantially. Unfortunately, however, the process may give rise to off-flavors due to diacetyl, the formation of which can be reduced with the aid of acetolactate converting enzymes.

Thus, in some embodiments, the processes of the invention provide for the production of alcoholic beverages with lower content of diacetyl, wherein the time required for producing the alcoholic beverages with lower content of diacetyl is reduced by at least 10%, or at least 20% or at least 30%, or at least 40%, or at least 50%, or at least 60%, or at least 70%, or at least 80%, or at least 90% when compared to a process without the use of the ALDC and/or ALDC derivative compositions described herein. In some embodiments, the processes of the invention provide for the production of alcoholic beverages with lower content of diacetyl when compared to a process without the use of the ALDC and/or ALDC derivative compositions described herein, wherein a maturation step is completely eliminated.

In some embodiments, the ALDC and/or ALDC derivative compositions described herein are used during a fermentation process (e.g. beer and/or wine and/or cider and/or perry and/or sake fermentation), such that the time required for the fermentation process is reduced by at least 10%, or at least 20% or at least 30%, or at least 40%, or at least 50%, or at least 60%, or at least 70%, or at least 80%, or at least 90%, when compared to a process without the use of the ALDC and/or ALDC derivative compositions described herein. In some embodiments, the processes of the invention provide for the production of alcoholic beverages with lower content of diacetyl when compared to a process without the use of the ALDC and/or ALDC derivative compositions described herein, wherein a maturation step is completely eliminated.

In some embodiments, the ALDC and/or ALDC derivative compositions described herein are used during a maturation or conditioning process (e.g. beer maturation/conditioning), such that the time required for the maturation or conditioning process is reduced by at least 10%, or at least 20% or at least 30%, or at least 40%, or at least 50%, or at least 60%, or at least 70%, or at least 80%, or at least 90%, when compared to a process without the use of the ALDC and/or ALDC derivative compositions described herein. In some embodiments, the processes of the invention provide for the production of alcoholic beverages with lower content of diacetyl when compared to a process without the use of the ALDC and/or ALDC derivative compositions described herein, wherein a maturation step is completely eliminated.

Further, in some embodiments, the processes described herein can be used to advantage for industrial preparation of ethanol as fermentation products are obtained without or practically without any content of diacetyl, which simplifies the distillation process, especially in case of azeotropic for the preparation of absolute ethanol, i.e. pure anhydrous ethanol.

In some embodiments, the invention provides methods for beer and/or wine and/or cider and/or perry and/or sake production comprising adding a composition comprising an ALDC enzyme and metal ion to a media (such as a fermentation and/or a maturation media) for the beer and/or wine and/or cider and/or perry and/or sake so that the metal ion is present in said media at a concentration of about 0.1 μM to about 500 μM, or about 0.1 μM to about 300 μM, or about 0.1 μM to about 50 μM, or about 1 μM to about 500 μM, or about 1 μM to about 300 μM, or about 6 μM to about 300 μM, or about 1 μM to about 100 μM, or about 1 μM to about 50 μM, or about 6 μM to about 50 μM, or about 6 μM to about 25 μM, or about 10 μM to about 150 mM, or about 20 μM to about 120 mM, or about 25 μM to about 100 mM, or about 25 μM to about 50 mM, or about 25 μM to about 20 mM, or about 25 μM to about 50 μM, or about 100 μM to about 20 mM, or about 250 μM to about 20 mM, or about 1 mM to about 20 mM, or about 1 mM to about 5 mM. In some embodiments, the metal ion is selected from the group consisting of $Zn^{2+}$, $Mg^{2+}$, $Mn^{2+}$, $Co^{2+}$, $Cu^{2+}$, $Ba^{2+}$, $Ca^{2+}$ and $Fe^{2+}$ and combinations thereof. In some embodiments, the metal ion is selected from the group consisting of $Zn^{2+}$, $Cu^{2+}$, and $Fe^{2+}$. In some embodiments, the metal ion is selected from the group consisting of $Zn^{2+}$, $Mn^{2+}$, and $Co^{2+}$. In some embodiments, the metal ion is $Zn^{2+}$ or $Mn^{2+}$. In some embodiments, the metal ion is $Zn^{2+}$. In some embodiments, the invention provides methods for beer and/or wine and/or cider and/or perry and/or sake production comprising adding a composition comprising an ALDC enzyme and zinc to a media (such as a fermentation and/or a maturation media) for the beer and/or wine and/or cider and/or perry and/or sake wherein said zinc is present in the composition at a concentration of about 0.25 mM to about 200 mM, such as about 1 mM to about 20 mM, or about 1 mM to about 5 mM. In some embodiments, the invention provides methods for beer and/or wine and/or cider and/or perry and/or sake production comprising adding a composition comprising an ALDC enzyme and zinc to a media (such as a fermentation and/or a maturation media) for the beer and/or wine and/or cider and/or perry and/or sake, wherein the molar ratio of zinc to ALDC enzyme that is higher than 1 such as 2:1, or 3:1, or 5:1, or 10:1, or 20:1 or 30:1, or 50:1, or 60:1. In some embodiments, the ALDC enzyme and said zinc are added during a fermentation process and/or a maturation process. In some embodiments, the ALDC enzyme is added at a concentration of about 0.01 g to about 10 g, or about 0.5 g to about 10 g, or about 1 g to about 5 g per hectoliter of beer and/or wine and/or cider and/or perry and/or sake ferment. As used herein the term "beer and/or wine and/or cider and/or perry and/or sake ferment" may be interchangeable with the term media. In some embodiments, the activity of said ALDC enzyme is in the range of 1000 to 2500 Units per mg of protein.

In some embodiments, the invention provides methods for beer and/or wine and/or cider and/or perry and/or sake production comprising adding a composition comprising an ALDC enzyme and metal ion to a media (such as a fermentation and/or a maturation media) for the beer and/or wine and/or cider and/or perry and/or sake, wherein the metal ion is present in said composition at a concentration of about 1 μM to about 200 mM, or about 100 μM to about 200 mM, and the composition comprising the ALDC enzyme and the metal ion are added at a concentration of about 0.01 g to about 10 g per hectoliter of beer and/or wine and/or cider and/or perry and/or sake ferment. In some embodiments, the invention provides methods for beer and/or wine and/or cider and/or perry and/or sake production comprising adding a composition comprising ALDC enzyme and metal ion to a media (such as a fermentation and/or a maturation media) for the beer and/or wine and/or cider and/or perry and/or sake, wherein the metal ion is present in said composition at a concentration of about 1 μM to about 200 mM, or about 100 μM to about 200 mM, and the composition comprising the ALDC enzyme and the metal ion are added at a concentration of about 0.5 g to about 10 g per hectoliter of beer and/or wine and/or cider and/or perry and/or sake ferment. In some embodiments, the invention provides methods for beer and/or wine and/or cider and/or perry and/or sake production comprising adding a composition comprising an ALDC enzyme and metal ion to a media (such as a fermentation and/or a maturation media) for the beer and/or wine and/or cider and/or perry and/or sake, wherein the metal ion is present in said composition at a concentration of about 1 μM to about 200 mM or about 100 μM to about 200 mM, and the composition comprising the ALDC enzyme and the metal ion are added at a concentration of about 1 g to about 5 g per hectoliter of beer and/or wine and/or cider and/or perry and/or sake ferment. In some embodiments, the invention provides methods for beer and/or wine and/or cider and/or perry and/or sake production comprising adding a composition comprising an ALDC enzyme and metal ion to a media (such as a fermentation and/or a maturation media) for the beer and/or wine and/or cider and/or perry and/or sake, wherein the metal ion is present in said composition at a concentration of about 1 μM to about 200 mM, or about 100 μM to about 200 mM, and the composition comprising the ALDC enzyme and the metal ion are added at a concentration of about 1 g to about 2 g per hectoliter of beer and/or wine and/or cider and/or perry and/or sake ferment. In some embodiments the metal ion is present in the composition at a concentration of about 1 mM to about 20 mM, or about 1 mM to about 10 mM, or about 1 mM to about 5 mM. In some embodiments, the metal ion is selected from the group consisting of $Zn^{2+}$, $Mg^{2+}$, $Mn^{2+}$, $Co^{2+}$, $Cu^{2+}$, $Ba^{2+}$, $Ca^{2+}$ and $Fe^{2+}$ and combinations thereof. In some embodiments, the metal ion is selected from the group consisting of $Zn^{2+}$, $Cu^{2+}$, and $Fe^{2+}$. In some embodiments, the metal ion is selected from the group consisting of $Zn^{2+}$, $Mn^{2+}$, and $Co^{2+}$. In some embodiments, the metal ion is $Zn^{2+}$ or $Mn^{2+}$. In some embodiments, the metal ion is $Zn^{2+}$. In some embodiments, the activity of said ALDC enzyme is in the range of 950 to 2500 Units per mg of protein or 1000 to 2500 Units per mg of protein or 1500 to 2500 Units per mg of protein.

In some embodiments, the invention provides methods for beer and/or wine and/or cider and/or perry and/or sake production comprising adding an ALDC enzyme and metal ion in a composition to a media (such as a fermentation and/or a maturation media) for the beer and/or wine and/or cider and/or perry and/or sake, wherein the molar ratio of the metal ion to the ALDC enzyme is higher than 1, and the composition comprising the ALDC enzyme and the metal ion are added at a concentration of about 0.01 g to about 10 g per hectoliter of beer and/or wine and/or cider and/or perry and/or sake ferment. In some embodiments, the invention provides methods for beer and/or wine and/or cider and/or perry and/or sake production comprising adding an ALDC enzyme and metal ion in a composition to a media (such as a fermentation and/or a maturation media) for the beer and/or wine and/or cider and/or perry and/or sake, wherein the molar ratio of the metal ion to the ALDC enzyme is higher than 1, and the composition comprising the ALDC enzyme and the metal ion are added at a concentration of about 0.5 g to about 10 g per hectoliter of beer and/or wine and/or cider and/or perry and/or sake ferment. In some embodiments, the invention provides methods for beer and/or wine and/or cider and/or perry and/or sake production comprising adding an ALDC enzyme and metal ion in a composition to a media (such as a fermentation and/or a maturation media) for the beer and/or wine and/or cider and/or perry and/or sake, wherein the molar ratio of the metal ion to the ALDC enzyme is higher than 1, and the composition comprising the ALDC enzyme and the metal ion are added at a concentration of about 1 g to about 5 g per hectoliter of beer and/or wine and/or cider and/or perry and/or sake ferment. In some embodiments, the invention provides methods for beer and/or wine and/or cider and/or perry and/or sake production comprising adding an ALDC enzyme and metal ion in a composition to a media (such as a fermentation and/or a maturation media) for the beer and/or wine and/or cider and/or perry and/or sake, wherein the molar ratio of the metal ion to the ALDC enzyme is higher than 1, and the composition comprising the ALDC enzyme and the metal ion are added at a concentration of about 1 g to about 2 g per hectoliter of beer and/or wine and/or cider and/or perry and/or sake ferment. In some embodiments, the molar ratio of the metal ion to the ALDC enzyme is 2:1, or 3:1, or 5:1, or 10:1, or 20:1 or 30:1, or 50:1, or 60:1, or higher. In some embodiments, the metal ion is selected from the group consisting of $Zn^{2+}$, $Mg^{2+}$, $Mn^{2+}$, $Co^{2+}$, $Cu^{2+}$, $Ba^{2+}$, $Ca^{2+}$ and $Fe^{2+}$ and combinations thereof. In some embodiments, the metal ion is selected from the group consisting of $Zn^{2+}$, $Cu^{2+}$, and $Fe^{2+}$. In some embodiments, the metal ion is selected from the group consisting of $Zn^{2+}$, $Mn^{2+}$, and $Co^{2+}$. In some embodiments, the metal ion is $Zn^{2+}$ or $Mn^{2+}$. In some embodiments, the metal ion is $Zn^{2+}$. In some embodiments, the activity of said ALDC enzyme is in the range of 950 to 2500 Units per mg of protein or 1000 to 2500 Units per mg of protein or 1500 to 2500 Units per mg of protein.

Production of ALDC Enzymes

In one aspect, the description relates to a nucleic acid capable of encoding an ALDC enzyme as described herein. In a further aspect, the description relates to an expression vector or plasmid comprising such a nucleic acid, or capable of expressing an ALDC enzyme as described herein. In one aspect, the expression vector or plasmid comprises a promoter derived from *Trichoderma* such as a *T. reesei* cbhI-derived promoter. In a further aspect, the expression vector or plasmid comprises a terminator derived from *Trichoderma* such as a *T. reesei* cbhI-derived terminator. In yet a further aspect, the expression vector or plasmid comprises one or more selective markers such as *Aspergillus nidulans* amdS and pyrG. In another aspect, the expression vector or plasmid comprises one or more telomere regions allowing for a non-chromosomal plasmid maintenance in a host cell.

In one aspect, the description relates to a host cell having heterologous expression of an ALDC enzyme as herein described. In a further aspect, the host cell is a fungal cell. In yet a further aspect, the fungal cell is of the genus *Trichoderma*. In yet a further aspect, the fungal cell is of the species *Trichoderma reesei* or of the species *Hypocrea jecorina*. In another aspect, the host cell comprises, preferably is transformed with, a plasmid or an expression vector as described herein.

In some embodiments, the host cell is a bacterial host cell such as *Bacillus*. In some embodiments the ALDC enzyme is produced by cultivation of a *Bacillus subtilis* strain containing a gene encoding and expressing an ALDC enzyme (e.g. ALDC of *Bacillus brevis*). Examples of such host cells and cultivation thereof are described in DK149335B.

Examples of suitable expression and/or integration vectors are provided in Sambrook et al. (1989) supra, and Ausubel (1987) supra, and van den Hondel et al. (1991) in Bennett and Lasure (Eds.) More Gene Manipulations In Fungi, Academic Press pp. 396-428 and U.S. Pat. No. 5,874,276. Reference is also made to the Fungal Genetics Stock Center Catalogue of Strains (FGSC, http://www.fgsc.net) for a list of vectors. Particularly useful vectors include vectors obtained from for example Invitrogen and Promega. Suitable plasmids for use in bacterial cells include pBR322 and pUC19 permitting replication in *E. coli* and pE194 for example permitting replication in *Bacillus*. Other specific vectors suitable for use in *E. coli* host cells include vectors such as pFB6, pBR322, pUC18, pUC100, pDONR™201, 10 pDONR™221, pENTR™, pGEM®3Z and pGEM®4Z.

Specific vectors suitable for use in fungal cells include pRAX, a general purpose expression vector useful in *Aspergillus*, pRAX with a glaA promoter, and in Hypocrea/*Trichoderma* includes pTrex3g with a cbh1 promoter.

In some embodiments, the host cells are fungal cells and optionally filamentous fungal host cells. The term "filamentous fungi" refers to all filamentous forms of the subdivision Eumycotina (see, Alexopoulos, C. J. (1962), Introductory Mycology, Wiley, New York). These fungi are characterized by a vegetative mycelium with a cell wall composed of chitin, cellulose, and other complex polysaccharides. The filamentous fungi of the present disclosure are morphologically, physiologically, and genetically distinct from yeasts. Vegetative growth by filamentous fungi is by hyphal elongation and carbon catabolism is obligatory aerobic. In the present disclosure, the filamentous fungal parent cell may be a cell of a species of, but not limited to, *Trichoderma* (e.g.,

*Trichoderma reesei*, the asexual morph of *Hypocrea jecorina*, previously classified as *T. longibrachiatum, Trichoderma viride, Trichoderma koningii, Trichoderma harzianum*) (Sheir-Neirs et al., Appl. Microbiol. Biotechnol. 20:46-53 (1984); ATCC No. 56765 and ATCC No. 26921), *Penicilliurn* sp., *Humicola* sp. (e.g., *H. insolens, H. lanuginosa* and *H. grisea*), *Chrysosporium* sp. (e.g., *C. lucknowense*), *Gliocladium* sp., *Aspergillus* sp. (e.g., *A. oryzae, A. niger, A sojae, A. japonicus, A. nidulans*, and *A. awamori*) (Ward et al., Appl. Microbiol. Biotechnol. 39:738-743 (1993) and Goedegebuur et al., Curr. Genet. 41:89-98 (2002)), *Fusarium* sp., (e.g., *F. roseum, F. graminum, F. cerealis, F. oxysporum*, and *F. venenatum*), *Neurospora* sp., (*N. crassa*), Hypocrea sp., *Mucor* sp. (*M. miehei*), *Rhizopus* sp., and *Emericella* sp. (see also, Innis et al., Science 228:21-26 (1985)). The term "*Trichoderma*" or "*Trichoderma* sp." or "*Trichoderma* spp." refer to any fungal genus previously or currently classified as *Trichoderma.*

In some embodiments, the host cells will be gram-positive bacterial cells. Non-limiting examples include strains of *Streptomyces* (e.g., *S. lividans, S. coelicolor*, and *S. griseus*) and *Bacillus*. As used herein, "the genus *Bacillus*" includes all species within the genus "*Bacillus*," as known to those of skill in the art, including but not limited to *B. subtilis, B. licheniformis, B. lentus, B. brevis, B. stearothermophilus, B. alkalophilus, B. amyloliquefaciens, B. clausii, B. halodurans, B. megaterium, B. coagulans, B. circulans, B. lautus*, and *B. thuringiensis*. It is recognized that the genus *Bacillus* continues to undergo taxonomical reorganization. Thus, it is intended that the genus include species that have been reclassified, including but not limited to such organisms as *B. stearothermophilus*, which is now named "*Geobacillus tearothermophilus.*"

In some embodiments, the host cell is a gram-negative bacterial strain, such as *E. coli* or *Pseudomonas* sp. In other embodiments, the host cells may be yeast cells such as *Saccharomyces* sp., *Schizosaccharomyces* sp., *Pichia* sp., or *Candida* sp. In other embodiments, the host cell will be a genetically engineered host cell wherein native genes have been inactivated, for example by deletion in bacterial or fungal cells. Where it is desired to obtain a fungal host cell having one or more inactivated genes known methods may be used (e.g., methods disclosed in U.S. Pat. Nos. 5,246,853, 5,475,101, and WO 92/06209). Gene inactivation may be accomplished by complete or partial deletion, by insertional inactivation or by any other means that renders a gene nonfunctional for its intended purpose (such that the gene is prevented from expression of a functional protein). In some embodiments, when the host cell is a *Trichoderma* cell and particularly a *T. reesei* host cell, the cbh1, cbh2, egl1 and egl2 genes will be inactivated and/or deleted. Exemplary *Trichoderma reesei* host cells having quad-deleted proteins are set forth and described in U.S. Pat. No. 5,847,276 and WO 05/001036. In other embodiments, the host cell is a protease deficient or protease minus strain. The term "protease deficient" or a "protease minus strain" as used herein refers to a host cell derived or derivable from a parental cell wherein the host cell comprises one or more genetic alterations that causes the host cells to produce a decreased amount of one or more proteases (e.g. functional proteases) when compared to the parental cell; preferably said host cell is deficient in one or more proteases selected from the group consisting of WprA, Vpr, Epr, IspA, Bpr, NprE, AprE, ampS, aprX, bpf, clpCP, clpEP, clpXP, codWX, lonA, lonB, nprB, map, mlpA, mpr, pepT, pepF, dppA, yqyE, tepA, yfiT, yflG, ymfF, ypwA, yrrN, yrrO, and ywaD. a variant host cell derived from a parental cell is provided, the variant host cell comprises one or more genetic alterations that causes cells of the variant strain to produce a decreased amount of one or more proteases when compared to the parental cell.

Introduction of a DNA construct or vector into a host cell includes techniques such as transformation; electroporation; nuclear microinjection; transduction; transfection, (e.g., lipofection-mediated and DEAE-Dextrin mediated transfection); incubation with calcium phosphate DNA precipitate; high velocity bombardment with DNA-coated microprojectiles; and protoplast fusion. General transformation techniques are known in the art (see, e.g., Ausubel et al. (1987) supra, chapter 9; and Sambrook et al. (1989) supra, and Campbell et al., *Curr. Genet.* 16:53-56 (1989)).

Transformation methods for *Bacillus* are disclosed in numerous references including Anagnostopoulos C. and J. Spizizen, *J. Bacteriol.* 81:741-746 (1961) and WO 02/14490.

Transformation methods for *Aspergillus* are described in Yelton et al., *Proc. Natl. Acad. Sci. USA* 81:1470-1474 (1984); Berka et al., (1991) in *Applications of Enzyme Biotechnology*, Eds. Kelly and Baldwin, Plenum Press (NY); Cao et al., *Protein Sci.* 9:991-1001 (2000); Campbell et al., *Curr. Genet.* 16:53-56 (1989), and EP 238 023. The expression of heterologous protein in *Trichoderma* is described in U.S. Pat. Nos. 6,022,725; 6,268,328; Harkki et al. *Enzyme Microb. Technol.* 13:227-233 (1991); Harkki et al., *BioTechnol.* 7:596-603 (1989); EP 244,234; EP 215,594; and Nevalainen et al., "The Molecular Biology of Trichoderma and its Application to the Expression of Both Homologous and Heterologous Genes", in Molecular Industrial Mycology, Eds. Leong and Berka, Marcel Dekker Inc., NY (1992) pp. 129-148). Reference is also made to WO96/00787 and Bajar et al., *Proc. Natl. Acad. Sci. USA* 88:8202-8212 (1991) for transformation of *Fusarium* strains.

In one aspect, the description relates to a method of isolating an ALDC enzyme as defined herein, the method comprising the steps of inducing synthesis of the ALDC enzyme in a host cell as defined herein having heterologous expression of said ALDC enzyme and recovering extracellular protein secreted by said host cell, and optionally purifying the ALDC enzyme. In a further aspect, the description relates to a method for producing an ALDC enzyme as defined herein, the method comprising the steps of inducing synthesis of the ALDC enzyme in a host cell as defined herein having heterologous expression of said ALDC enzyme, and optionally purifying the ALDC enzyme. In a further aspect, the description relates to a method of expressing an ALDC enzyme as defined herein, the method comprising obtaining a host cell as defined herein, or any suitable host cells as known by a person of ordinary skill in the art, and expressing the ALDC enzyme from said host cell, and optionally purifying the ALDC enzyme. In another aspect, the ALDC enzyme as defined herein is the dominant secreted protein.

In some embodiments, metal ions such as $Zn^{2+}$, $Mg^{2+}$, $Mn^{2+}$, $Co^{2+}$, $Cu^{2+}$, $Ba^{2+}$, $Ca^{2+}$ and $Fe^{2+}$ and combinations thereof are added to the media (such as a cultivation and/or a fermentation and/or a maturation media) during and/or after ALDC production to increase the recovered yields from microorganisms.

In some embodiments, the invention provides a cultivation media for an ALDC producing host cell comprising a metal ion at a concentration of about 1 μM to about 1 mM. In some embodiments, the invention provides a cultivation media for an ALDC producing host cell comprising a metal ion at a concentration of about 25 μM to about 150 μM. In some embodiments, the invention provides a cultivation media for an ALDC producing host cell comprising a metal ion at a concentration of about 25 μM to about 50 μM. In some embodiments, the invention provides a cultivation media for an ALDC producing host cell comprising a metal ion at a concentration of about 30 μM to about 40 μM. In some embodiments, the invention provides a cultivation media for an ALDC producing host cell comprising a metal ion at a concentration of about 40 μM to about 150 μM. In some embodiments, the invention provides a cultivation media for an ALDC producing host cell comprising a metal ion at a concentration of about 60 μM to about 150 μM. In some embodiments, the metal ion is selected from the group consisting of $Zn^{2+}$, $Mg^{2+}$, $Mn^{2+}$, $Co^{2+}$, $Cu^{2+}$, and $Fe^{2+}$ and combinations thereof. In some embodiments, the metal ion is selected from the group consisting of $Zn^{2+}$, $Cu^{2+}$, and $Fe^{2+}$. In some embodiments, the metal ion is selected from the group consisting of $Zn^{2+}$, $Mn^{2+}$, and $Co^{2+}$. In some embodiments, the metal ion is $Zn^{2+}$ or $Mn^{2+}$. In some embodiments, the metal ion is $Zn^{2+}$. In some embodiments, the activity of said ALDC enzyme is in the range of 950 to 2500 Units per mg of protein or 1000 to 2500 Units per mg of protein or 1500 to 2500 Units per mg of protein. The term "ALDC producing host cell" as used herein refers to a host cell capable of expressing ALDC enzyme when said host cell is cultured under conditions permitting the expression of the nucleic acid sequence encoding ALDC. The nucleic acid sequence encoding ALDC enzyme may be heterologous or homologous to the host cell. In some embodiments, the ALDC producing host cell is *Bacillus subtilis*. In some embodiments, the ALDC producing host cell is *Bacillus subtilis* comprising a gene encoding and expressing ALDC enzyme wherein the ALDC enzyme comprises an amino acid sequence having at least 70%, 75%, 80%, 85%, 90%, 95%, 97%, 98%, 99% or 100% identity with SEQ ID NO: 2, SEQ ID NO: 3, SEQ ID NO: 5, SEQ ID NO: 7, SEQ ID NO: 8, or any functional fragment thereof. In some embodiments, the ALDC producing host cell is *Bacillus subtilis* comprising a nucleic acid sequence encoding ALDC wherein said nucleic acid sequence encoding ALDC has at least 70%, 75%, 80%, 85%, 90%, 95%, 97%, 98%, 99% or 100% identity with SEQ ID NO: 1, SEQ ID NO: 4, SEQ ID NO: 6 or any functional fragment thereof. In some embodiments, the ALDC producing host cell is *Bacillus subtilis* comprising a gene encoding ALDC derived from *Bacillus brevis*.

EXAMPLES

The present disclosure is described in further detail in the following examples, which are not in any way intended to limit the scope of the disclosure as claimed. The attached figures are meant to be considered as integral parts of the specification and description of the disclosure. The following examples are offered to illustrate, but not to limit the claimed disclosure.

Example 1—Heterologous Expression of Acetolactate Decarboxylase, aldB

The *Brevibacillus brevis* (which may be referred to as *Bacillus brevis*) acetolactate decarboxylases (ALDC) aldB gene was previously identified (Diderichsen et al., *J Bacteriol.* (1990) 172(8): 4315), with the sequence set forth as UNIPROT Accession No. P23616.1. The sequence of this gene, aldB, is depicted in SEQ ID NO:1. The nucleotides highlighted in bold and underlined are the nucleotides which encode the signal peptide.

sets forth the nucleotide sequence of the aldB gene:

SEQ ID NO: 1 atgaaaaaaaatatcatcacttctatcacatctctggctctggttgccgggctgtctttgactgcttttgcagctacaacggctactgtac cagcaccacctgccaagcaggaatccaaacctgcggttgccgctaatccggcaccaaaaaatgtactgtttcaatactcaacgatcaatgca ctcatgcttggacagtttgaaggggacttgactttgaaagacctgaagctgcgaggcgatatggggcttggtaccatcaatgatctcgatgga gagatgattcagatgggtacaaaattctaccagatcgacagcaccggaaaattatcggagctgccagaaagtgtgaaaactccatttgcggt tactacacatttcgagccgaaagaaaaaactacattaaccaatgtgcaagattacaatcaattaacaaaaatgcttgaggagaaatttgaaaac aagaacgtcttttatgccgtaaagctgaccggtacctttaagatggtaaaggctagaacagttccaaaacaaaccagaccttatccgcagctg actgaagtaaccaaaaaacaatccgagtttgaatttaaaaatgttaagggaaccctgattggcttctatacgccaaattatgcagcagccctga atgttcccggattccatctccacttcatcacagaggataaaacaagtggcggacacgtattaaatctgcaatttgacaacgcgaatctggaaat ttctccgatccatgagtttgatgtacaattgccgcacacagatgattttgcccactctgatctgacacaagttactactagccaagtacaccaag ctgagtcagaaagaaaataa sets forth an example of a nucleotide sequence encoding an acetolactate decarboxylase-
the nucleotides highlighted in bold and underlined are the nucleotides which encode
the signal peptide:

SEQ ID NO: 6 atgaaaaaaaatatcatcacttctatcacatctctggctctcgttgccgggctgtctttgactgcttttgcagctacaacggctactgta ccagcaccacctgccaagcaggaatccaaacctgtggttgccgctaatccggcaccaaaaaatgtactgtttcaatactcaacgat caatgcactcatgcttggacagtttgaaggggacttgactttgaaagacctgaagctacgaggcgatatggggcttggtaccatcaa tgatctcgatggagagatgattcagatgggtacaaaattctaccagatcgacagcaccggaaaattatccgagctgccagaaagtgtgaaaa ctccatttgcggttactacacatttcgagccgaaagaaaaaactacattaaccaatgtgcaagattacaatcaattaacaaaaatgcttgagga gaaatttgaaaacaagaacgtcttttatgccgtaaagctgaccggtacctttaagatggtaaaggctagaacagttccaaaacaaaccagacc -continued ttatccgcagctgactgaagtaaccaaaaaacaatccgagtttgaatttaaaaatgttaagggaaccctgattggcttctatacgccaaattatg cagcagccctgaatgttcccggattccatctccacttcatcacagaggataaaacaagtggcggacacgtattaaatctgcaatttgacaacg cgaatctggaaatttctccgatccatgagtttgatgtacaattgccgcacacagatgattttgcccactctgatctgacacaagttactactag ccaagtacaccaagctgagtcagaaagaaaataa The proenzyme encoded by the aldB gene is depicted in SEQ ID NO: 2. At the N-terminus, the protein has a signal peptide with a length of 24 amino acids as predicted by SignalP-NN (Emanuelsson et al., *Nature Protocols* (2007) 2: 953-971). This signal peptide sequence is underlined and is in bold in SEQ ID NO:2. The presence of a signal peptide indicates that this acetolactate decarboxylase, aldB is a secreted enzyme. The sequence of the predicted, fully processed mature chain (aldB, 261 amino acids) is depicted in SEQ ID NO: 3.

A map of the vector containing the aldB gene (RIHI-aldB) is shown in FIG. 1.

The nucleotide mature sequence of the aldB gene in plasmid RIHI-aldB is depicted in SEQ ID NO:4.

gctacaacggctactgtaccagcaccacctgccaagcaggaatccaaacc tgcggttgccgctaatccggcaccaaaaaatgtactgtttcaatactcaa sets forth the amino acid sequence of the acetolactate decarboxylase (ALDC) precursor aldB:

SEQ ID NO: 2

MKKNIITSITSLALVAGLSLTAFAATTATVPAPPAKQESKPAVAANPAPKNVLFQYSTI

NALMLGQFEGDLTLKDLKLRGDMGLGTINDLDGEMIQMGTKFYQIDSTGKLSELPESV

KTPFAVTTHFEPKEKTTLTNVQDYNQLTKMLEEKFENKNVFYAVKLTGTFKMVKARTV

VLNLQFDNANLEISPIHEFDVQLPHTDDFAHSDLTQVTTSQVHQAESERK sets forth an example of an amino acid sequence of the acetolactate decarboxylase (ALDC) precursor aldB-the signal peptide sequence is underlined and is in bold:

SEQ ID NO: 7

MKKNIITSITSLALVAGLSLTAFAATTATVPAPPAKQESKPVVAANPAPKNVLFQYSTI

NALMLGQFEGDLTLKDLKLRGDMGLGTINDLDGEMIQMGTKFYQIDSTGKLSELPESV

KTPFAVTTHFEPKEKTTLTNVQDYNQLTKMLEEKFENKNVFYAVKLTGTFKMVKARTV

PKQTRPYPQLTEVTKKQSEFEFKNVKGTLIGFYTPNYAAALNVPGFHLHFITEDKTSGGH

VLNLQFDNANLEISPIHEFDVQLPHTDDFAHSDLTQVTTSQVHQAESERK sets forth the predicted amino acid sequence of the mature acetolactate decarboxylase (ALDC) aldB (261 amino acids):

SEQ ID NO: 3

ATTATVPAPPAKQESKPAVAANPAPKNVLFQYSTINALMLGQFEGDLTLKDLKLRGDM

GLGTINDLDGEMIQMGTKFYQIDSTGKLSELPESVKTPFAVTTHFEPKEKTTLTNVQDYN

QLTKMLEEKFENKNVFYAVKLTGTFKMVKARTVPKQTRPYPQLTEVTKKQSEFEFKNV

DDFAHSDLTQVTTSQVHQAESERK sets forth an example of the predicted amino acid sequence of the mature acetolactate decarboxylase (ALDC) aldB (261 amino acids):

SEQ ID NO: 8

ATTATVPAPPAKQESKPVVAANPAPKNVLFQYSTINALMLGQFEGDLTLKDLKLRGDM

GLGTINDLDGEMIQMGTKFYQIDSTGKLSELPESVKTPFAVTTHFEPKEKTTLTNVQDYN

QLTKMLEEKFENKNVFYAVKLTGTFKMVKARTVPKQTRPYPQLTEVTKKQSEFEFKNV

DDFAHSDLTQVTTSQVHQAESERK

The aldB gene from the strain *Brevibacillus brevis* encoding an acetolactate decarboxylases enzyme (ALDC) was produced in *B. subtilis* using an integrated expression cassette consisting of the *B. subtilis* aprE promoter, the *B. subtilis* aprE signal peptide sequence, the mature aldB and a BPN' terminator. This cassette was cloned in the head to head orientation with respect to the expression cassette and the aldB expression cassette introduced into *B. subtilis* by homologous recombination.

-continued cgatcaatgcactcatgcttggacagtttgaaggggacttgactttgaaa gacctgaagctgcgaggcgatatggggcttggtaccatcaatgatctcga tggagagatgattcagatgggtacaaaattctaccagatcgacagcaccg gaaaattatcggagctgccagaaagtgtgaaaactccatttgcggttact -continued

```
acacatttcgagccgaaagaaaaaactacattaaccaatgtgcaagatta

caatcaattaacaaaaatgcttgaggagaaatttgaaaacaagaacgtct

tttatgccgtaaagctgaccggtacttttaagatggtaaaggctagaaca

gttccaaaacaaaccagaccttatccgcagctgactgaagtaaccaaaaa

acaatccgagtttgaatttaaaaatgttaagggaaccctgattggcttct

atacgccaaattatgcagcagccctgaatgttcccggattccatctccac

ttcatcacagaggataaaacaagtggcggacacgtattaaatctgcaatt

tgacaacgcgaatctggaaatttctccgatccatgagtttgatgttcaat

tgccgcacacagatgattttgcccactctgatctgacacaagttactact

agccaagtacaccaagctgagtcagaaagaaaa
```

The amino acid sequence of the aldB precursor protein expressed from plasmid RIHI-aldB is depicted in SEQ ID NO:5.

*vrskklwisllfaltliftmafsnmsaqa*ATTATVPAPPAKQESKPA

VAANPAPKNVLFQYSTINALMLGQFEGDLTLKDLKLRGDMGLGTINDLDG

EMIQMGTKFYQIDSTGKLSELPESVKTPFAVTTHFEPKEKTTLTNVQDYN

QLTKMLEEKFENKNVFYAVKLTGTFKMVKARTVPKQTRPYPQLTEVTKKQ

SEFEFKNVKGTLIGFYTPNYAAALNVPGFHLHFITEDKTSGGHVLNLQFD

NANLEISPIHEFDVQLPHTDDFAHSDLTQVTTSQVHQAESERK

The signal peptide sequence is in bold lowercase italics in SEQ ID NO:5.

Small Scale Culture Conditions

To produce aldB, a *B. subtilis* strain transformant containing aldB expression cassette was cultured in 15 mL Falcon tubes for 5 hours in TSB (broth) with 300 ppm beta-chloro-D-alanine (CDA), and 300 μL of this pre-culture was added to a 500 mL flask filled with 30 mL of cultivation media (described below) supplemented with 300 ppm CDA and 50 μM $Zn^{2+}$. The flasks were incubated for 24, 48 and 72 hours at 33° C. with constant rotational mixing at 180 rpm. Cultures were harvested by centrifugation at 14500 rpm for 20 minutes in conical tubes. The culture supernatants were used for protein determination and assays. The cultivation media was an enriched semi-defined media based on MOPs buffer, with urea as major nitrogen source, maltrin as the main carbon source.

Fed-Batch Fermentation Conditions

To produce aldB, a *B. subtilis* strain transformant containing aldB expression cassette was cultured in a 250 mL flasks containing 30 mL of complex medium with 300 ppm beta-chloro-D-alanine (CDA). The flask was incubated for 6 hours at 37° C. with constant rotational mixing at 180 rpm.

The culture was transferred to a stirred fermentor containing 7 liters of sterilized media components as described in table 1 below. Temperature was controlled to 37° C.; pH was controlled to 7.5 using ammonium hydroxide as alkaline titrant; dissolved oxygen was maintained at 40% or higher by maintaining an airflow of 7 liter/min, a constant overpressure of 1 bar and adjusting stirring rate. When initial glucose was exhausted a feeding profile feeding a 60% glucose solution into the fermentor was initiated (initial feeding rate was 20 g/h linearly increasing to 32.8 g/h over 7 hours and kept constant at that rate until fermentation termination).

Total fermentation time was 44 hours.

TABLE 1

Media recipe for ALDC fermentation

| Component | Recipe Conc (g/kg) |
|---|---|
| Soy Meal | 50.0 |
| Citric acid | 0.10 |
| Magnesium sulfate heptahydrate | 2.29 |
| Potassium Phosphate, Mono Basic | 5.44 |
| Ferrous sulfate, heptahydrate | 0.029 |
| Manganese Sulfate Mono hydrate | 0.051 |
| Zinc sulphate heptahydrate | 0.001 |
| Glucose mono hydrate | 1.10 |
| Anti foam agent | 3.00 |

Example 2—Protein Determination Methods

Protein Determination by Stain Free Imager Criterion

Protein was quantified by SDS-PAGE gel and densitometry using Gel Doc™ EZ imaging system. Reagents used in the assay: Concentrated (2×) Laemmli Sample Buffer (Bio-Rad, Catalogue #161-0737); 26-well XT 4-12% Bis-Tris Gel (Bio-Rad, Catalogue #345-0125); protein markers "Precision Plus Protein Standards" (Bio-Rad, Catalogue #161-0363); protein standard BSA (Thermo Scientific, Catalogue #23208) and SimplyBlue Safestain (Invitrogen, Catalogue #LC 6060. The assay was carried out as follow: In a 96 well-PCR plate 504, diluted enzyme sample were mixed with 50 μL sample buffer containing 2.7 mg DTT. The plate was sealed by Microseal 'B' Film from Bio-Rad and was placed into PCR machine to be heated to 70° C. for 10 minutes. After that the chamber was filled by running buffer, gel cassette was set. Then 10 μL of each sample and standard (0.125-1.00 mg/mL BSA) was loaded on the gel and 5 μL of the markers were loaded. After that the electrophoresis was run at 200 V for 45 min. Following electrophoresis the gel was rinsed 3 times 5 min in water, then stained in Safestain overnight and finally destained in water. Then the gel was transferred to Imager. Image Lab software was used for calculation of intensity of each band. By knowing the protein amount of the standard sample, the calibration curve can be made. The amount of sample can be determined by the band intensity and calibration curve. The protein quantification method was employed to prepare samples of aldB acetolactate decarboxylases enzyme used for assays shown in subsequent Examples.

Example 3—Activity Assay Method

Spectrophotometric Assay of α-Acetolactate Decarboxylase

α-Acetolactate decarboxylase (ALDC) catalyses the decarboxylation of α-acetolactate to acetoin. The reaction product acetoin can be quantified colourimetrically. Acetoin mixed with α-naphtol and creatine forms a characteristic red color absorbing at OD522 nm. ALDC activity was calculated based on $OD_{522\ nm}$ and an acetoin calibration curve. The assay was carried out as follows: 20 mM acetolactate substrate was prepared by mixing 100 μL ethyl-2-acetoxy-2-methylacetoacetate (Sigma, Catalogue #220396) with 3.6 mL 0.5 M NaOH at 10° C. for 10 min. 20 mL 50 mM MES pH 6.0 was added, pH was adjusted to pH 6.0 and volume adjusted to 25 mL with 50 mM MES pH 6.0. 80 μL 20 mM acetolactate substrate was mixed with 20 μL enzyme sample diluted in 50 mM MES, pH 6.0, 0.6 M NaCl, 0.05% BRIJ 35 and 0.01% BSA. The substrate/enzyme mixture was incubated at 30° C. for 10 min. Then 16 μL substrate/enzyme mixture was transferred to 200 μL 1 M NaOH, 1.0% α-naphtol (Sigma, Catalogue #33420) and 0.1% creatine (Sigma, Catalogue #C3630). The substrate/enzyme/color reagent mixture was incubated at 30° C. for 20 min and then $OD_{522\ nm}$ was read. One unit of ALDC activity is defined as the amount of enzyme which produces 1 μmole acetoin per minute under the conditions of the assay.

Example 4—Zinc Influence on Activity of ALDC

The Presence of $Zn^{2+}$ During Shake Flask Fermentation $ZnSO_4$ was added to the cultivation media for small scale fermentations as described in Example 1 at concentrations ranging from 0 mM to 800 μM. aldB. *B. subtilis* transformant containing aldB expression cassette was cultured in 15 mL Falcon tubes for 5 hours in TSB (broth) with 300 ppm beta-chloro-D-alanine (CDA), and 300 μL of this pre-culture was added to a each 500 mL flask filled with 30 mL of cultivation media supplemented with 300 ppm CDA and containing 0, 5, 25, 50, 100, 200, 400 and 800 μM $Zn^{2+}$. The flasks were incubated for 24 and 48 hours at 33° C. with constant rotational mixing at 180 rpm. Cultures were harvested by centrifugation at 14500 rpm for 20 minutes in conical tubes. The culture supernatants were used for protein determination and ALDC activity assays (Table 2 and 3). It is clearly seen that increasing the concentration of $Zn^{2+}$ in the fermentation media increased the total ALDC activity and specific activity of expressed aldB enzyme.

TABLE 2

ALDC activity of aldB fermentation samples with varying levels of $Zn^{2+}$ after 24 and 48 hours of fermentation

| | | ALDC activity | |
|---|---|---|---|
| | $ZnSO_4$ in sample μM | 24 hours of fermentation U/mL | 48 hours of fermentation U/mL |
| aldB | 0 | 298.6 | 235.3 |
| | 5 | 371.9 | 354.8 |
| | 25 | 533.9 | 808.0 |
| | 50 | 606.4 | 965.3 |
| | 100 | 633.4 | 668.8 |
| | 200 | 617.6 | 629.5 |
| | 400 | 691.1 | 488.5 |
| | 800 | 428.1 | 474.0 |

TABLE 3

ALDC activity, aldB protein and specific activity of aldB fermentation samples with varying levels of $Zn^{2+}$ after 48 hours of fermentation

| | $ZnSO_4$ in sample μM | ALDC activity U/mL | AldB protein mg/mL | Specific activity U/mg |
|---|---|---|---|---|
| aldB | 0 | 235.3 | 0.626 | 375.9 |
| | 5 | 354.8 | 0.736 | 482.1 |
| | 25 | 808.0 | 1.437 | 562.3 |
| | 50 | 965.3 | 1.573 | 609.9 |
| | 100 | 668.8 | 0.957 | 698.9 |

Example 5—Modulation of the Specific Activity of aldB Samples

Zinc Dose Response of ALDC at 50° C.

Figure 2:
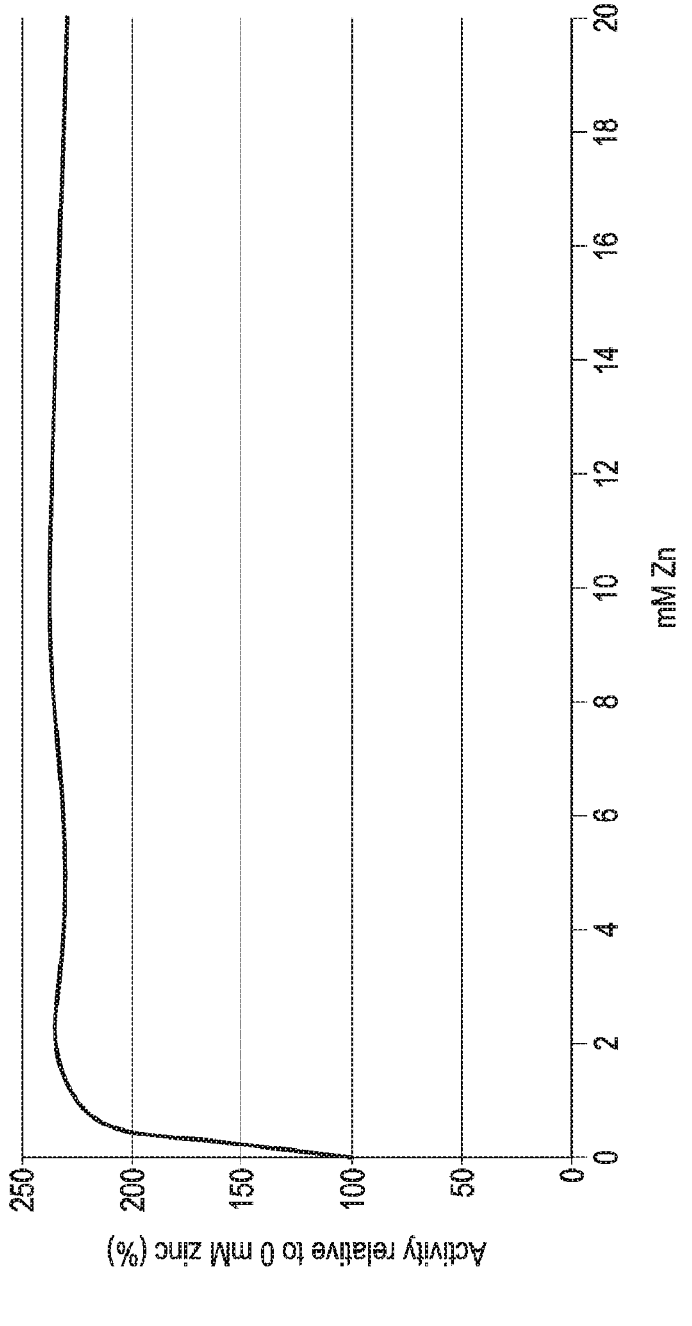
FIG. 2 shows a graph depicting the activity of ALDC relative to 0 mM zinc vs concentration of zinc in mM.

$ZnSO_4$ was added to ALDC fermentation sample to produce concentrations ranging from 0 mM to 20 mM. The samples were kept at 50° C. for 60 min and then activity was measured as described in Example 3. Relative to a sample with no zinc added samples with >0.5 mM zinc had activity >200% higher. FIG. 2 shows results.

Example 6—Modulation of the Specific Activity of aldB Ferment

Figure 3A:
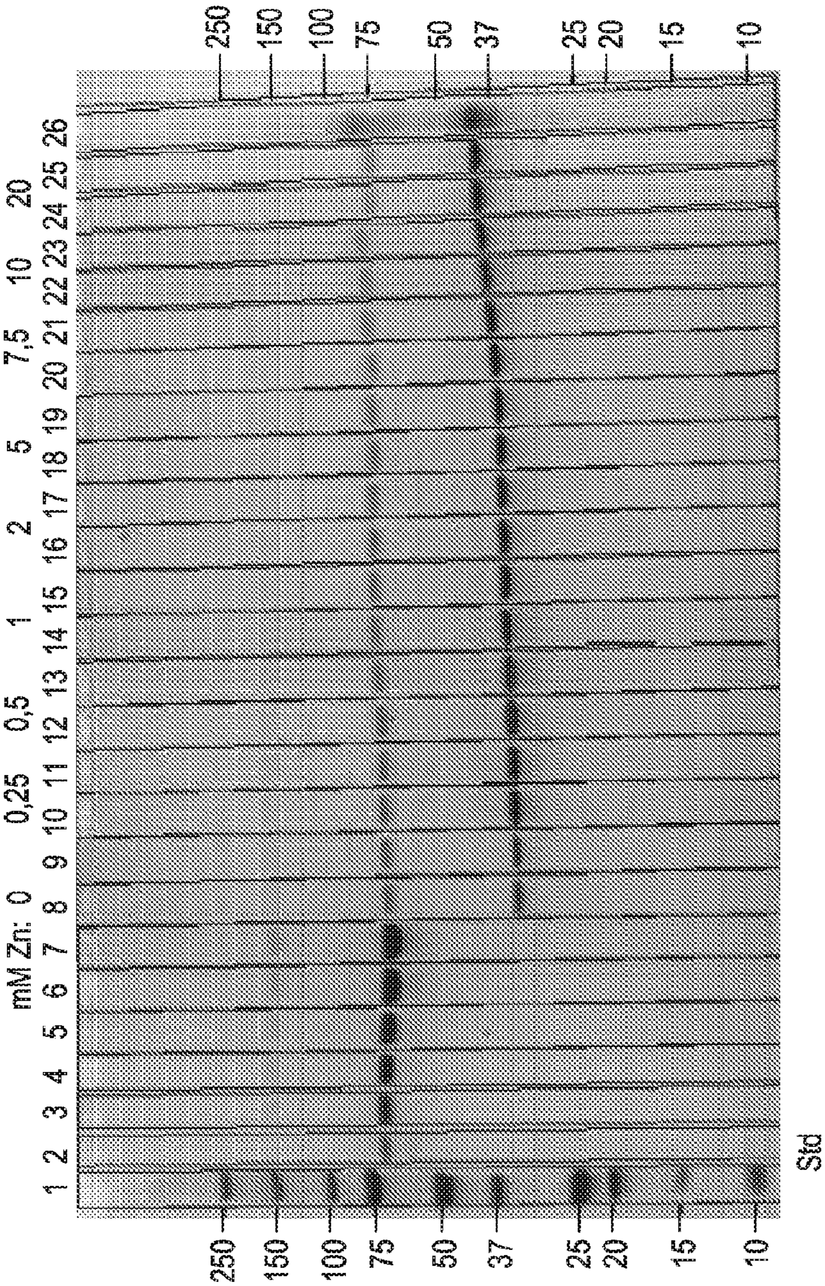
FIGS. 3A-3B show SDS-PAGE with aid B samples containing varying concentration of $ZnSO_4$. Gel A—Lane 1) Molecular weight marker; Lane 2-7) BSA standard; Lane 8-9) AldB with 0 mM $ZnSO_4$; Lane 10-11) AldB with 0.25 mM $ZnSO_4$; Lane 12-13) AldB with 0.5 mM $ZnSO_4$; Lane 14-15) AldB with 1.0 mM $ZnSO_4$; Lane 16-17) AldB with 2 mM $ZnSO_4$; Lane 18-19) AldB with 5 mM $ZnSO_4$; Lane 20-21) AldB with 7.5 mM $ZnSO_4$; Lane 22-23) AldB with 10 mM $ZnSO_4$ and Lane 24-25) AldB with 20 mM $ZnSO_4$. Gel B—Lane 1) Molecular weight marker; Lane 2-7) BSA standard; Lane 8-11) AldB with 0 mM $ZnSO_4$; Lane 12-15) AldB with 20 mM $ZnSO_4$; Lane 16-17) AldB with 40 mM $ZnSO_4$; Lane 18-19) AldB with 60 mM $ZnSO_4$; Lane 20-21) AldB with 80 mM $ZnSO_4$; Lane 22-23) AldB with 100 mM $ZnSO_4$ and Lane 24-25) AldB with 120 mM $ZnSO_4$.
Figure 3B:
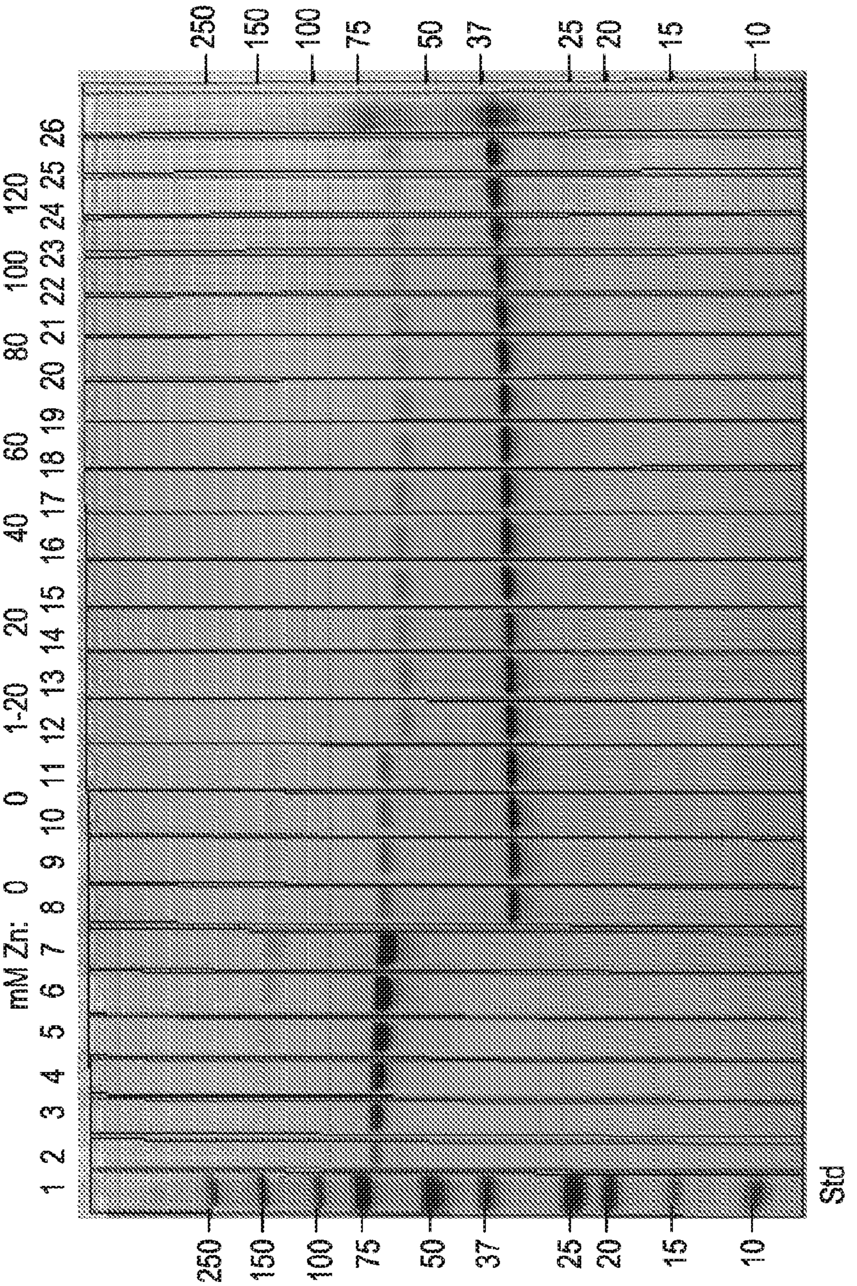

AldB activity was produced as described in (Example 1) and activity determined as described in (Example 3). An AldB ferment sample was diluted in 50 mM MES pH 6.0, 0.6 M NaCl, 0.05% Brij, 0.01% BSA (bovine serum albumin) to proximately 1000 U/mL and then incubated with varying concentration of $ZnSO_4$ in the following steps: 0, 0.25, 0.5, 1, 2, 5, 7.5, 10, 20, 40, 60, 80, 100, 120 mM. All samples were incubated at 4° C. for 68 hours, then centrifuged and supernatant analyzed for activity and protein by Criterion SDS-PAGE analysis. The results of the SDS-PAGE analysis is shown in FIG. 3 and the determined activity, protein concentration and specific activity are given in table 4. It can be seen that the ALDC activity increases with increasing concentration of $ZnSO_4$ in the sample until approximately 5-10 mM from where it is more or less constant with the higher concentrations of $ZnSO_4$. The concentration of aldB protein in the sample was determined to be more or less constant in all samples indicating an apparent increase in the specific activity from 968 U/mg in the sample without $ZnSO_4$ up to 2200-2400 U/mg in samples with 5 mM $ZnSO_4$ or more after incubation.

TABLE 4

ALDC activity, aldB protein concentration and specific activity of aldB sample incubated with $ZnSO_4$ at 4° C. for 68 hours.

| | $ZnSO_4$ in sample mM | ALDC activity U/mL | AldB protein mg/mL | Specific activity U/mg |
|---|---|---|---|---|
| aldB | 0 | 556 | 0.57 | 968 |
| | 0.25 | 875 | 0.63 | 1387 |
| | 0.5 | 949 | 0.63 | 1512 |
| | 1 | 1058 | 0.59 | 1792 |
| | 2 | 1271 | 0.60 | 2124 |
| | 5 | 1411 | 0.60 | 2354 |
| | 7.5 | 1485 | 0.64 | 2311 |
| | 10 | 1520 | 0.64 | 2368 |
| | 20 | 1492 | 0.64 | 2344 |
| | 40 | 1499 | 0.67 | 2239 |
| | 60 | 1495 | 0.64 | 2345 |
| | 80 | 1500 | 0.65 | 2324 |
| | 100 | 1607 | 0.64 | 2520 |
| | 120 | 1520 | 0.69 | 2209 |

Example 7—Purification of aldB

Production of aldB in *B. subtilis* was carried out as described in example (1). Fermentation media was clarified by centrifugation (4000 rpm at 15 min.) and filtration (VacuCap 90, 0.2 μm). The sample was desalted on PD10 column, prepared as described by the manufacturer and equilibrated with 20 mM Tris/HCl, pH 8.0. The eluate was kept on ice afterwards before further purified by anion exchange chromatography on a Source 15Q XK26/15. The column was equipped on an ÄKTA explorer system used for protein purification and according to the method described by the manufacturer (GE healthcare, USA—Cat. No. 18-1112-41).

The column was prepared as described by the manufacturer and equilibrated with 20 mM Tris/HCl, pH 8.0 (buffer A). The desalted sample was applied to the column at a flow rate of 5 mL/min and the column was washed with buffer A. The bound proteins were eluted with a linear gradient of 0-0.30 M NaCl in 20 mM Tris/HCl, pH 8.0 (7 mL/min, 40 min). During the entire run, fractions of approx. 10-20 mL were collected.

Fractions from purification were analysed by SDS-PAGE using Xcell Mini-cell and according to the method described by the manufacturer (Invitrogen, USA—Cat. No. EI0001) using: Nu-PAGE gel (Invitrogen, USA—Cat. No. NP0321), MES running buffer (Invitrogen, USA—Cat. No. NP0002), See Blue standard marker (Invitrogen, USA—Cat. No. LC5925) and Stained with Coomasie Brilliant-Blue.

Figure 4:
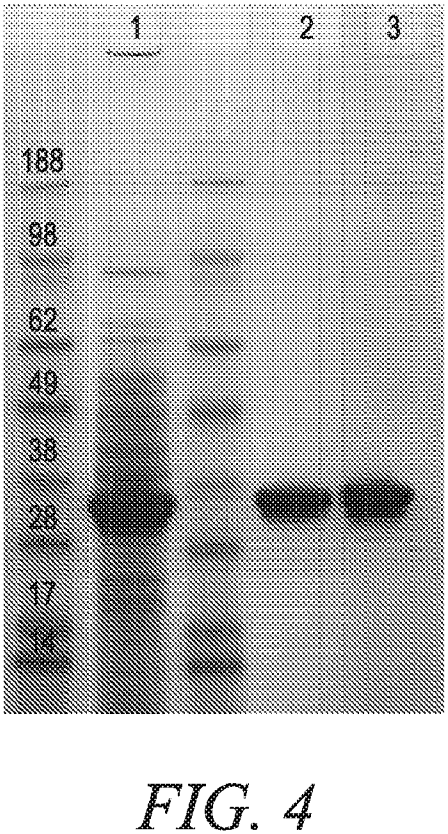
FIG. 4 shows SDS-PAGE with purification of aldB produced in *B. subtilis.* Lane 1) crude aldB ferment; 2-3) purified aldB from Source15Q. Molecular weight marker is shown to the left and in-between lane 1 and 2.

AldB was observed to bind at the Source 15Q column and was eluted with approximately 30 mM NaCl. AldB fractions were collected, concentrated (on a 10 kDa OF Vivaspin) and desalted in 25 mM HEPES buffer containing 150 mM NaCl, pH 8.0. The estimated purity of aldB was above 95% and the result of SDS-page analysis of the purified aldB is shown in FIG. 4.

Example 8—Modulation of the Specific Activity of Purified aldB

The purified aldB protein was stripped of divalent ions by incubation of aldB (approximately 2 mg/mL) with 20 mM EDTA in 0.2× assay buffer (50 mM MES pH 6.0, 0.6 M NaCl, 0.05% Brij, 0.01% BSA) at 37° C. overnight. The EDTA treated material was desalted on a PD10 column prepared as described by the manufacturer and equilibrated with 50 mM MES pH 6.0, 0.6 M NaCl, 0.05% Brij, 0.01% BSA. ALDC activity and the concentration of AldB protein in the sample before and after EDTA treatment and the desalting column were determined as described in example (2 and 3) and the results are shown in table 5.

TABLE 5

ALDC activity, aldB protein concentration and specific activity of purified aldB before and after the EDTA-desalting procedure.

| | ALDC Activity U/mL | AldB protein concentration mg/mL | Specific Activity U/mg |
|---|---|---|---|
| AldB purified | 5187 | 5.6 | 928 |
| AldB purified - EDTA treated and desalted | 9 | 1.0 | 9 |

50 µL of the EDTA treated and desalted aldB sample was mixed with 450 µL of 0.2× assay buffer (50 mM MES pH 6.0, 0.6 M NaCl, 0.05% Brij, 0.01% BSA) with varying $ZnSO_4$ in the step: 0, 0.05, 0.1, 0.5, 1, 2, 5, 10 and 20 mM respectively. Samples were incubated at 37° C. overnight. The samples were centrifuged at 13000 rpm for 10 min and ALDC activity and the concentration of AldB protein were determined in the supernatant. The results are shown in table 6. It can be seen that the ALDC activity increases with increasing concentration of $ZnSO_4$ during incubation. The concentration of aldB protein in the sample was determined to be constant in all samples indicating an increase in the specific activity from 2 U/mg of aldB in the sample without $ZnSO_4$ up to 1800 U/mg aldB in samples with 5 mM $ZnSO_4$ or more after incubation.

TABLE 6

ALDC activity, aldB protein concentration and specific activity of purified aldB before and after incubation with $ZnSO_4$.

| Concentration of ZnSO4 in 0.2X assay bufer mM | Final concentration of ZnSO4 mM | ALDC Activity U/mL | aldB protein concentration mg/mL | Specific activity U/mg |
|---|---|---|---|---|
| 0 | 0 | 0.1 | 0.092 | 2 |
| 0.05 | 0.045 | 4.4 | 0.092 | 48 |
| 0.1 | 0.09 | 26.1 | 0.092 | 283 |
| 0.5 | 0.45 | 147.1 | 0.092 | 1599 |
| 1 | 0.9 | 157.7 | 0.092 | 1714 |
| 2 | 1.8 | 157.9 | 0.092 | 1716 |
| 5 | 4.5 | 166.4 | 0.092 | 1809 |
| 10 | 9 | 174.6 | 0.092 | 1898 |
| 20 | 18 | 173.5 | 0.092 | 1886 |

In addition, 20 µL of the EDTA treated and desalted aldB sample was mixed with 180 µL of 50 mM MES pH 6.0 supplemented with either 10 mM $ZnSO_4$, $MnSO_4$ or $CoCl_2$ respectively. Samples were incubated at 37° C. and assayed after 45 minutes, 1 day, 2 days and 3 days. Results are shown in table 7. The activity increased for incubation with all three divalent ions in the order $Zn^{2+}$, $Mn^{2+}$ and $Co^{2+}$ compared to the control (addition of $H_2O$). After 45 min the activity was shown to decrease over time. The addition of $Zn^{2+}$, $Mn^{2+}$ and $Co^{2+}$ all resulted in an increased stability (activity) after 3 days compared to the control with addition of $H_2O$. The residual activity measured after 3 days relative to the start were 76.9%, 73.5% and 70.7% upon addition of $Zn^{2+}$, $Mn^{2+}$ and $Co^{2+}$ compared to 56.0% obtained with $H_2O$, as shown in table 7.

TABLE 7

ALDC activity after incubation at pH 6.0 with $MnSO_4$, $CoCl_2$ or $ZnSO_4$ at various times.

| | Activity U/mL | | | |
|---|---|---|---|---|
| | H2O | $Mn^{2+}$ | $Co^{2+}$ | $Zn^{2+}$ |
| 45 min | 21.8 | 217.3 | 101.8 | 319.7 |
| 1 day | 18.9 | 219.6 | 90.5 | 288.5 |
| 2 days | 22.5 | 216.2 | 95.2 | 295.4 |
| 3 days | 12.2 | 153.6 | 74.8 | 245.7 |

Example 9—Reduction in Diacetyl and 2,3-Pentanedione During Beer Fermentation by Use of aldB with Different Specific ALDC Activity The objective of this analysis was to test different formulation variants of aldB (acetolactate decarboxylase) ability to reduce development of diacetyl and 2,3-pentanedione (Vicinal di-ketones, VDK) during a 7 days fermentation at 14° C.

Pure Malt Brew Analysis 1100 g Munton's Light Malt Extract (Batch XB 35189, expiry date 24 May 2014) extract was dissolved in 3000 mL warm tapwater (45° C.). This slurry was stirred for about 10 min until the liquid was homogeneous and the pH was adjusted to 5.2 with 2.5 M sulphuric acid. To the slurry was added 10 pellets of Bitter hops from Hopfenveredlung, St. Johann: Alpha content of 16.0% (EBC 7.7 0 specific HPLC analysis, Jan. 10, 2013), then split in 500 mL blue-cap bottles and boiled for 1 hour to ensure protein precipitation and avoid potential microbial contamination. The filtered malt extract (wort) was sampled for specific gravity and Free Amino Nitrogen (FAN) determination. The final wort had an initial Specific Gravity of 1048 (i.e. 12°Plato). 200 g of the filtered wort were added to a 500 mL conical flask (Fermenting Vessel; FV), and then cooled to 13° C. Each conical flask was dosed with 0.5% W34/70 (Weihenstephan) freshly produced yeast (1.0 g yeast per 200 g wort). The enzymes were dosed on similar ALDC activity (0.03 U/mL wort, 8 ALDC Units per 200 g wort). The control fermentation vessel with no enzyme received an amount of deionized water corresponding to the amount of enzyme sample.

The wort samples were fermented in 500 mL conical flasks under standardised laboratory test conditions at 14° C. with gentle agitation at 150 rpm in an orbital incubator. When weight loss was less than 0.25 g over 24 hours, fermentation temperature was decreased to 7° C. Fermentation was stopped after 7 days in total. 10 mL samples were taken out for diacetyl and 2,3-pentanedione analysis two times a day, preferably with 11 to 14 hours in between; at the end of fermentation only 1 sample per day was taken. Yeast was allowed to settle before take-out and each sample was cooled at 10° C. for 10 minutes and then centrifuged at 4000 rpm for 10 minutes at 8° C. to sediment any residual yeast. The supernatant was separated from the yeast sediment and samples for GC analysis were added 0.5 g NaCl per mL of sample. This slurry was transferred to a headspace vial and heat-treated at 65° C. for 30 minutes before analysis for diacetyl and 2,3-pentanedione were carried out by gas chromatography with mass spectrometric detection (GCMS).

Analyses were carried out at an Agilent 6890N/5973N GC with CombiPAL headspace autosampler and MSChemStation acquisition and analysis software. The samples were equilibrated at 70° C. for 10 minutes before 500 μl of the gas phase above the sample was injected onto a J&W 122-0763 DB-1701 column (60 m×0.25 mmID×1 μm). The injection temperature was 260° C. and the system was operated with a constant helium flow of 2 mL/min. The oven temperature was: 50° C. (2 min), 160° C. (20° C./min), 220° C. (40° C./min), hold 2 min. MS detection were made with 500 μL at a split ratio of 5:1 at selected ions. All sample were run in duplicates and standards were made using tap water with the addition of diacetyl or 2,3-pentanedione.

The concentration of a compound is calculated as $$\text{Compound}\ (\text{mg}/L) = RF \times \frac{\text{Area}}{1000 \times W_s}$$

where,

RF is the response factor of acetic acid

Area is the GC-area of acetic acid $W_s$ is the amount of sample used (in mL)

The limit of diacetyl quantification was determined to 0.016 mg/L and the limit of 2,3-pentanedione quantification was determined to 0.012 mg/L.

To check that addition of ALDC enzymes did not influence the Real Degree of Fermentation (RDF) and the produced alcohol by volume: RDF was measured using an Anton Paar (DMA 5000) following Standard Instruction Brewing, 23.8580-B28 and alcohol by Standard Instruction Brewing, 23.8580-B28.

Real degree of fermentation (RDF) value may be calculated according to the equation below:

$$RDF(\%) = \left(1 - \frac{RE}{{}^{\circ}P_{initial}}\right) \times 100$$

Where: RE=real extract=$(0.1808 \times {}^{\circ}P_{initial}) + (0.8192 \times {}^{\circ}P_{final})$, ${}^{\circ}P_{initial}$ is the specific gravity of the standardised worts before fermentation and ${}^{\circ}P_{final}$ the specific gravity of the fermented worts expressed in degree Plato.

In the present context, Real degree of fermentation (RDF) was determined from the specific gravity and alcohol concentration.

Specific gravity and alcohol concentration was determined on the fermented samples using a Beer Alcolyzer Plus and a DMA 5000 Density meter (both from Anton Paar, Gratz, Austria). Based on these measurements, the real degree of fermentation (RDF) value was calculated according to the equation below:

$$RDF(\%) = \frac{OE - E(r)}{OE} \times 100$$

Where: E(r) is the real extract in degree Plato (°P) and OE is the original extract in °P.

The ability to reduce development of diacetyl and 2,3-pentanedione (Vicinal di-ketones, VDK) during a 7 days fermentation at 14° C. was studied by addition of aldB with different specific ALDC activity (obtained by varying the $ZnSO_4$ concentration in the sample) is given in table 8. The aldB variant constitute: A) a crude preparation of aldB, B) a crude preparation of aldB including 20 mM $ZnSO_4$ added to the clarified broth and C) a crude preparation of aldB including 50 μM $ZnSO_4$ added to the fermentation media and 20 mM $ZnSO_4$ into the clarified broth.

TABLE 8

ALDC activity, aldB protein concentration and specific activity of aldB sample A, B and C.

| | ALDC actiytity U/mL | aldB protein mg/mL | Specific ALDC activity U/mg |
|---|---|---|---|
| aldB variant A | 426 | 0.463 | 919 |
| aldB variant B | 511 | 0.463 | 1103 |
| aldB variant C | 719 | 0.463 | 1552 |

The enzymes variants were dosed on similar ALDC activity 0.03 U/mL wort resulting in a different concentration of aldB protein in the wort, as seen in table 9. The calculated aldB protein concentration in the wort was 33.4, 28.0 and 19.9 μg/L wort with addition of variant A, B and C respectively.

TABLE 9

ALDC activity and aldB protein in wort with addition of aldB variant A, B and C.

| | ALDC actiytity U/mL | Amount sample for predilution g | Volume predilution mL | Activity in wort U/mL | AldB protein in wort μg/l |
|---|---|---|---|---|---|
| AldB variant A | 426 | 0.721 | 50 | 0.03 | 33.4 |
| AldB variant B | 511 | 0.604 | 50 | 0.03 | 28.0 |
| AldB variant C | 719 | 0.430 | 50 | 0.03 | 19.9 |

Figure 5:
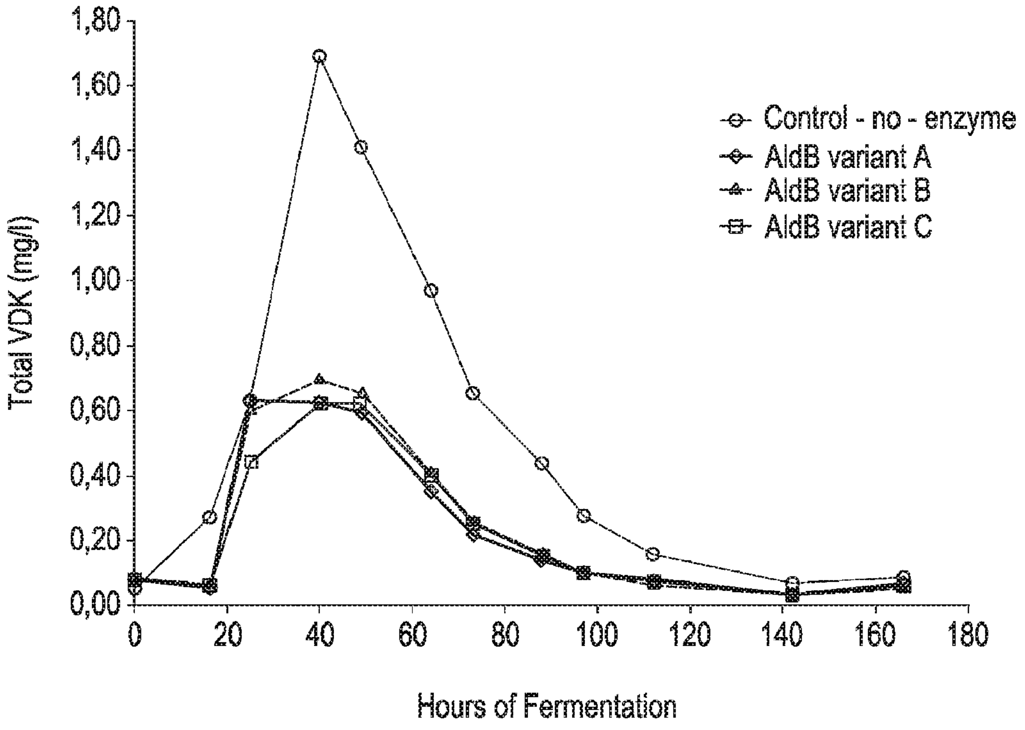
FIG. 5 shows development of vicinal diketones (VDK) during malt-based fermentations in the presence or absence of 0.03 U/mL wort aldB enzyme variants with different specific activity: A) 919 U/mg, B) 1103 U/mg and C) 1552 U/mg aldB. The VDK development (sum of diacetyl and 2,3 pentanedione) was followed during the 7 days of fermentation at 14° C. The average VDK values are calculated from duplicate samples and labels are shown as insert in figure.

The fermentations were conducted and VDK development analysed as described above. Fermentations with enzyme were compared to a control without any enzyme added. The development of VDK is shown in FIG. 5.

All three aldB variants reduced the VDK development during fermentation compared to control. The data suggest that the three variants performed very similar, however with less increase in VDK during the fermentation period from 20 to 40 hours for variant C compared to A and B, but this is close to the relative standard deviation of the analysis (RSD of 7.5%). The relative reduction in VDK after 40 hours of fermentation was 63.1%, 58.8% and 63.2% for variant A, B and C respectively. In addition, the fermentation time required to reach threshold level of 0.1 mg/ml VDK or lower, was observed to be approximately 112 hours for all three variants. Thus, the higher specific activity of variant C compared to A or B may enable similar VDK reduction with less aldB protein.

Example 10—Reduction in Diacetyl and 2,3-Pentanedione by aldB During Beer Fermentation with Various Concentration of Zinc in the Wort The objective of this analysis was to test reduction of diacetyl and 2,3-pentanedione (Vicinal di-ketones, VDK) by aldB during a 4 days fermentation at 14° C. in presence of various level of $ZnSO_4$ in the wort.

Figure 6:
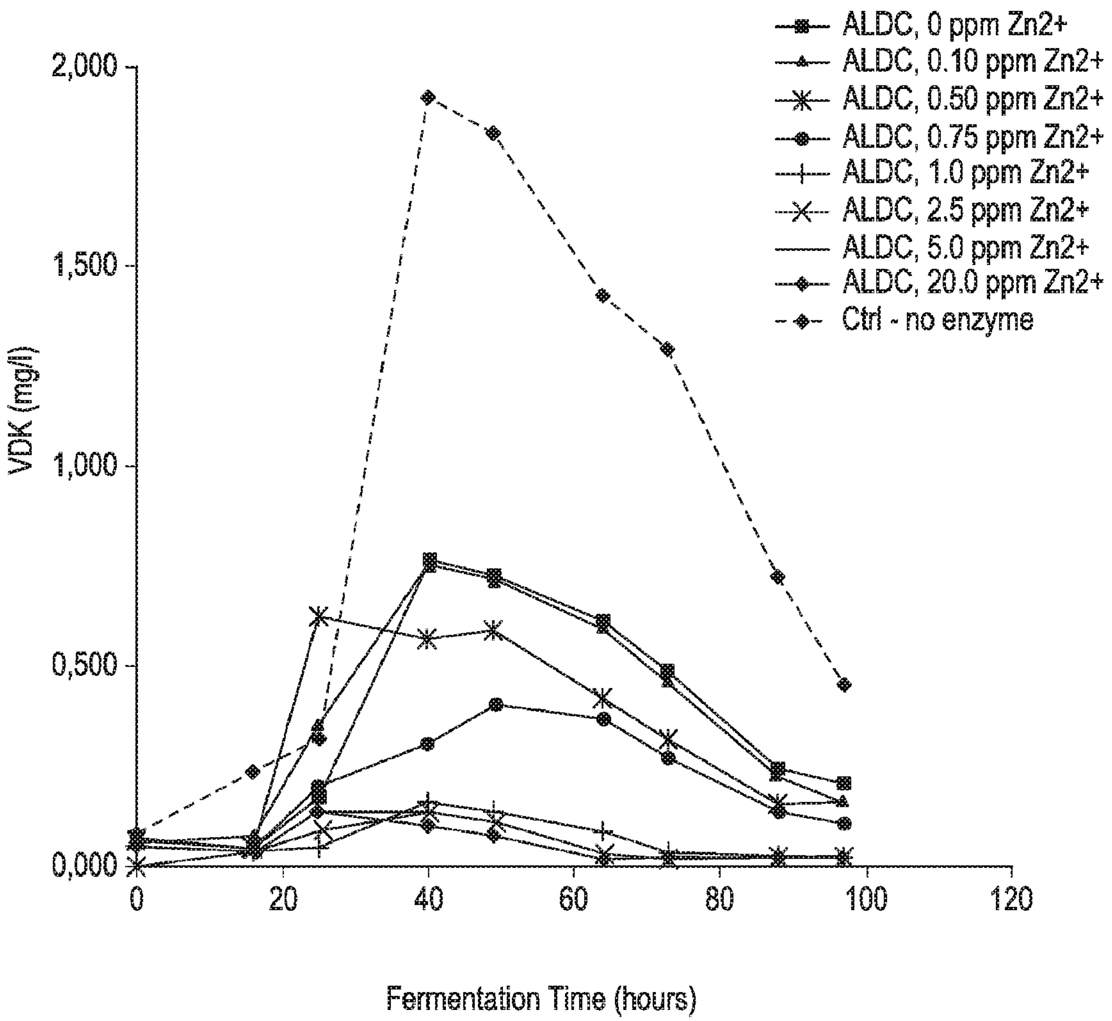
FIG. 6 shows VDK development in presence aldB enzyme (0.04 U/mL wort) during malt-based fermentations with different levels of $Zn^{2+}$ in the wort (see labels). The VDK development (sum of diacetyl and 2,3-pentanedione) was followed during the 7 days of fermentation at 14° C. The average VDK values are calculated from duplicate samples and labels are shown as insert in figure.

The brew analysis setup was as described in example 9. A stock solution of $ZnSO_4$ was made in cooled wort (0.686 g in 1000 mL wort) and applied to the wort samples (prepared as described in example 9) before fermentation resulting in the following $Zn^{2+}$ concentrations 0, 0.1, 0.5, 0.75, 1, 2.5, 5.0 and 20.0 ppm respectively. ALDC enzyme and yeast were subsequently added to the samples. An ALDC enzymes preparation were dosed similarly to all samples (0.04 U/mL wort, corresponding to 8 ALDC units per 200 g of wort). Each conical fermentation flask was dosed with 0.5% W34/70 (Weihenstephan) freshly produced yeast (1.0 g yeast per 200 g of wort) and analyses were carried out as described in example 9. Fermentations with enzyme were compared to a control without any enzyme added. The development of VDK is shown in FIG. 6.

All aldB treated samples provided less increase in the VDK development during fermentation compared to control. Increasing the concentration of $Zn^{2+}$ in the samples resulted in less and less increase in VDK generation. Especially increasing the concentration of $Zn^{2+}$ to 0.5 ppm or more greatly affected the enzymatic activity to avoid generation of VDK. Supplementing the wort with 1 ppm $Zn^{2+}$ or more ensured a VDK level below the flavor threshold of 0.1 mg/L throughout the whole fermentation period.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

The invention claimed is:

1. A method of preparing an acetolactate decarboxylase (ALDC) enzyme preparation, the method comprising the steps of:

culturing a *Bacillus subtilis* host cell comprising an expression cassette comprising a *Bacillus subtilis* aprE promoter and a *Bacillus subtilis* aprE signal peptide operably linked to a heterologous *Brevibacillus brevis* ALDC gene, in a cultivation medium supplemented with zinc at a concentration of 60 μM to 150 μM, whereby the host cell secretes the ALDC enzyme into the cultivation medium; and removing the host cell from the cultivation medium, thereby producing a cell-free ALDC enzyme preparation.

2. The method of claim 1, further comprising the step of purifying or concentrating the ALDC enzyme.

* * * * *

SEQUENCE LISTING

```
Sequence total quantity: 8
SEQ ID NO: 1            moltype = DNA  length = 858
FEATURE                 Location/Qualifiers
source                  1..858
                        mol_type = other DNA
                        organism = Brevibacillus brevis
SEQUENCE: 1
atgaaaaaaa atatcatcac ttctatcaca tctctggctc tggttgccgg gctgtctttg  60
actgcttttg cagctacaac ggctactgta ccagcaccac ctgccaagca ggaatccaaa  120
cctgcggttg ccgctaatcc ggcaccaaaa aatgtactgt ttcaatactc aacgatcaat  180
gcactcatgc ttggacagtt tgaaggggac ttgactttga aagacctgaa gctgcgaggc  240
gatatggggc ttggtaccat caatgatctc gatggagaga tgattcagat gggtacaaaa  300
ttctaccaga tcgacagcac cggaaaatta tcggagctgc cagaaagtgt gaaaactcca  360
tttgcggtta ctacacattt cgagccgaaa gaaaaaacta cattaaccaa tgtgcaagat  420
tacaatcaat taacaaaaat gcttgaggag aaatttgaaa acaagaacgt cttttatgcc  480
gtaaagctga ccggtacctt taagatggta aaggctagaa cagttccaaa acaaaccaga  540
ccttatccgc agctgactga agtaaccaaa aaacaatccg agtttgaatt taaaaatgtt  600
aagggaaccc tgattggctt ctatacgcca aattatgcag cagccctgaa tgttcccgga  660
ttccatctcc acttcatcac agaggataaa acaagtggcg gacacgtatt aaatctgcaa  720
tttgacaacg cgaatctgga aatttctccg atccatgagt ttgatgtaca attgccgcac  780
acagatgatt ttgcccactc tgatctgaca caagttacta ctagccaagt acaccaagct  840
gagtcagaaa gaaaataa                                                858

SEQ ID NO: 2            moltype = AA  length = 285
FEATURE                 Location/Qualifiers
source                  1..285
                        mol_type = protein
                        organism = Brevibacillus brevis
SEQUENCE: 2
MKKNIITSIT SLALVAGLSL TAFAATTATV PAPPAKQESK PAVAANPAPK NVLFQYSTIN  60
```

```
ALMLGQFEGD LTLKDLKLRG DMGLGTINDL DGEMIQMGTK FYQIDSTGKL SELPESVKTP  120
FAVTTHFEPK EKTTLTNVQD YNQLTKMLEE KFENKNVFYA VKLTGTFKMV KARTVPKQTR  180
PYPQLTEVTK KQSEFEFKNV KGTLIGFYTP NYAAALNVPG FHLHFITEDK TSGGHVLNLQ  240
FDNANLEISP IHEFDVQLPH TDDFAHSDLT QVTTSQVHQA ESERK                  285

SEQ ID NO: 3          moltype = AA  length = 261
FEATURE               Location/Qualifiers
source                1..261
                      mol_type = protein
                      organism = Brevibacillus brevis
SEQUENCE: 3
ATTATVPAPP AKQESKPAVA ANPAPKNVLF QYSTINALML GQFEGDLTLK DLKLRGDMGL  60
GTINDLDGEM IQMGTKFYQI DSTGKLSELP ESVKTPFAVT THFEPKEKTT LTNVQDYNQL  120
TKMLEEKFEN KNVFYAVKLT GTFKMVKART VPKQTRPYPQ LTEVTKKQSE FEFKNVKGTL  180
IGFYTPNYAA ALNVPGFHLH FITEDKTSGG HVLNLQFDNA NLEISPIHEF DVQLPHTDDF  240
AHSDLTQVTT SQVHQAESER K                                            261

SEQ ID NO: 4          moltype = DNA  length = 783
FEATURE               Location/Qualifiers
misc_feature          1..783
                      note = mature sequence of the aldB gene in plasmid RIHI-aldB
source                1..783
                      mol_type = other DNA
                      organism = synthetic construct
SEQUENCE: 4
gctacaacgg ctactgtacc agcaccacct gccaagcagg aatccaaacc tgcggttgcc  60
gctaatccgg caccaaaaaa tgtactgttt caatactcaa cgatcaatgc actcatgctt  120
ggacagtttg aaggggactt gactttgaaa gacctgaagc tgcgaggcga tatggggctt  180
ggtaccatca atgatctcga tggagagatg attcagatgg gtacaaaatt ctaccagatc  240
gacagcaccg gaaaattatc ggagctgcca gaaagtgtga aaactccatt tgcggttact  300
acacatttcg agccgaaaga aaaaactaca ttaaccaatg tgcaagatta caatcaatta  360
acaaaaatgc ttgaggagaa atttgaaaac aagaacgtct tttatgccgt aaagctgacc  420
ggtactttta agatggtaaa ggctagaaca gttccaaaac aaaccagacc ttatccgcag  480
ctgactgaag taaccaaaaa acaatccgag tttgaattta aaaatgttaa gggaaccctg  540
attggcttct atacgccaaa ttatgcagca gccctgaatg ttcccggatt ccatctccac  600
ttcatcacag aggataaaac aagtggcgga cacgtattaa atctgcaatt tgacaacgcg  660
aatctggaaa tttctccgat ccatgagttt gatgttcaat tgccgcacac agatgatttt  720
gcccactctg atctgacaca agttactact agccaagtac accaagctga gtcagaaaga  780
aaa                                                                783

SEQ ID NO: 5          moltype = AA  length = 290
FEATURE               Location/Qualifiers
REGION                1..290
                      note = aldB precursor protein expressed from plasmid
                       RIHI-aldB
source                1..290
                      mol_type = protein
                      organism = synthetic construct
SEQUENCE: 5
VRSKKLWISL LFALTLIFTM AFSNMSAQAA TTATVPAPPA KQESKPAVAA NPAPKNVLFQ  60
YSTINALMLG QFEGDLTLKD LKLRGDMGLG TINDLDGEMI QMGTKFYQID STGKLSELPE  120
SVKTPFAVTT HFEPKEKTTL TNVQDYNQLT KMLEEKFENK NVFYAVKLTG TFKMVKARTV  180
PKQTRPYPQL TEVTKKQSEF EFKNVKGTLI GFYTPNYAAA LNVPGFHLHF ITEDKTSGGH  240
VLNLQFDNAN LEISPIHEFD VQLPHTDDFA HSDLTQVTTS QVHQAESERK             290

SEQ ID NO: 6          moltype = DNA  length = 858
FEATURE               Location/Qualifiers
misc_feature          1..858
                      note = sequence encoding an acetolactate decarboxylase
source                1..858
                      mol_type = other DNA
                      organism = synthetic construct
SEQUENCE: 6
atgaaaaaaa atatcatcac ttctatcaca tctctggctc tcgttgccgg gctgtctttg  60
actgcttttg cagctacaac ggctactgta ccagcaccac ctgccaagca ggaatccaaa  120
cctgtggttg ccgctaatcc ggcaccaaaa aatgtactgt ttcaatactc aacgatcaat  180
gcactcatgc ttggacagtt tgaaggggac ttgactttga aagacctgaa gctacgaggc  240
gatatggggc ttggtaccat caatgatctc gatggagaga tgattcagat gggtacaaaa  300
ttctaccaga tcgacagcac cggaaaatta tccgagctgc cagaaagtgt gaaaactcca  360
tttgcggtta ctacacattt cgagccgaaa gaaaaaacta cattaaccaa tgtgcaagat  420
tacaatcaat taacaaaaat gcttgaggag aaatttgaaa acaagaacgt cttttatgcc  480
gtaaagctga ccggtacctt taagatggta aaggctagaa cagttccaaa acaaaccaga  540
ccttatccgc agctgactga agtaaccaaa aaacaatccg agtttgaatt taaaaatgtt  600
aagggaaccc tgattggctt ctatacgcca aattatgcag cagccctgaa tgttcccgga  660
ttccatctcc acttcatcac agaggataaa acaagtggcg gacacgtatt aaatctgcaa  720
tttgacaacg cgaatctgga aatttctccg atccatgagt ttgatgtaca attgccgcac  780
acagatgatt ttgcccactc tgatctgaca caagttacta ctagccaagt acaccaagct  840
gagtcagaaa gaaaataa                                                858
```

-continued

```
SEQ ID NO: 7            moltype = AA  length = 285
FEATURE                 Location/Qualifiers
REGION                  1..285
                        note = sequence of acetolactate decarboxylase (ALDC)
                         precursor aldB
source                  1..285
                        mol_type = protein
                        organism = synthetic construct
SEQUENCE: 7
MKKNIITSIT SLALVAGLSL TAFAATTATV PAPPAKQESK PVVAANPAPK NVLFQYSTIN  60
ALMLGQFEGD LTLKDLKLRG DMGLGTINDL DGEMIQMGTK FYQIDSTGKL SELPESVKTP  120
FAVTTHFEPK EKTTLTNVQD YNQLTKMLEE KFENKNVFYA VKLTGTFKMV KARTVPKQTR  180
PYPQLTEVTK KQSEFEFKNV KGTLIGFYTP NYAAALNVPG FHLHFITEDK TSGGHVLNLQ  240
FDNANLEISP IHEFDVQLPH TDDFAHSDLT QVTTSQVHQA ESERK                 285

SEQ ID NO: 8            moltype = AA  length = 261
FEATURE                 Location/Qualifiers
REGION                  1..261
                        note = predicted amino acid sequence of the mature
                         acetolactatedecarboxylase (ALDC) aldB
source                  1..261
                        mol_type = protein
                        organism = synthetic construct
SEQUENCE: 8
ATTATVPAPP AKQESKPVVA ANPAPKNVLF QYSTINALML GQFEGDLTLK DLKLRGDMGL  60
GTINDLDGEM IQMGTKFYQI DSTGKLSELP ESVKTPFAVT THFEPKEKTT LTNVQDYNQL  120
TKMLEEKFEN KNVFYAVKLT GTFKMVKART VPKQTRPYPQ LTEVTKKQSE FEFKNVKGTL  180
IGFYTPNYAA ALNVPGFHLH FITEDKTSGG HVLNLQFDNA NLEISPIHEF DVQLPHTDDF  240
AHSDLTQVTT SQVHQAESER K                                           261
```